(12) United States Patent
Hsia et al.

(10) Patent No.: US 8,562,976 B2
(45) Date of Patent: *Oct. 22, 2013

(54) CO-ENZYME Q10 FORMULATIONS AND METHODS OF USE

(75) Inventors: Sung Lan Hsia, Miami, FL (US); Niven Rajin Narain, Cambridge, MA (US); Jie Li, Miami, FL (US); Kathryn J. Russell, Sarasota, FL (US); Karrune V. Woan, Wellington, FL (US); Indushekhar Persaud, Homestead, FL (US)

(73) Assignee: University of Miami, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/366,224

(22) Filed: Feb. 3, 2012

(65) Prior Publication Data

US 2012/0201801 A1  Aug. 9, 2012

Related U.S. Application Data

(63) Continuation of application No. 10/597,378, filed as application No. PCT/US2005/001581 on Jan. 21, 2005, now Pat. No. 8,147,825.

(60) Provisional application No. 60/538,319, filed on Jan. 22, 2004.

(51) Int. Cl.
*A61K 38/43* (2006.01)

(52) U.S. Cl.
USPC ....................................... 424/94.1

(58) Field of Classification Search
USPC ....................................... 424/94.1
See application file for complete search history.

(56) References Cited

U.S. PATENT DOCUMENTS

| | | |
|---|---|---|
| 4,483,873 A | 11/1984 | Ohashi et al. |
| 4,515,736 A | 5/1985 | Deamer |
| 4,525,350 A | 6/1985 | Casey et al. |
| 4,636,381 A | 1/1987 | Takada et al. |
| 4,654,373 A | 3/1987 | Bertelli |
| 4,824,669 A | 4/1989 | Folkers et al. |
| 4,895,727 A | 1/1990 | Allen |
| 5,015,483 A | 5/1991 | Haynes et al. |
| 5,362,494 A | 11/1994 | Zysman et al. |
| 5,378,461 A | 1/1995 | Neigut |
| 5,527,789 A | 6/1996 | Nyce |
| 5,602,184 A | 2/1997 | Myers et al. |
| 5,603,958 A | 2/1997 | Morein et al. |
| 5,605,930 A | 2/1997 | Samid |
| 5,651,991 A | 7/1997 | Sugiyama et al. |
| 5,700,482 A | 12/1997 | Frederiksen et al. |
| 5,719,303 A | 2/1998 | Yoshida et al. |
| 5,770,222 A | 6/1998 | Unger et al. |
| 5,876,737 A | 3/1999 | Schonrock et al. |
| 5,889,062 A | 3/1999 | Hoppe et al. |
| 5,891,465 A | 4/1999 | Keller et al. |
| 5,912,272 A | 6/1999 | Hoppe et al. |
| 5,944,012 A | 8/1999 | Pera |
| 5,962,243 A | 10/1999 | Brown et al. |
| 6,005,086 A | 12/1999 | Evans et al. |
| 6,048,886 A | 4/2000 | Neigut |
| 6,071,495 A | 6/2000 | Unger et al. |
| 6,093,706 A | 7/2000 | Zeligs |
| 6,093,743 A | 7/2000 | Lai et al. |
| 6,184,353 B1 | 2/2001 | Evans et al. |
| 6,228,891 B1 | 5/2001 | Enzmann et al. |
| 6,261,575 B1 | 7/2001 | Hoppe et al. |
| 6,348,506 B2 | 2/2002 | Sneed |
| 6,372,234 B1 | 4/2002 | Deckers et al. |
| 6,416,957 B1 | 7/2002 | Evans et al. |
| 6,417,233 B1 | 7/2002 | Sears et al. |
| 6,441,050 B1 | 8/2002 | Chopra |
| 6,461,593 B1 | 10/2002 | Hanioka et al. |
| 6,465,517 B1 | 10/2002 | Van Der Zee |
| 6,468,552 B1 | 10/2002 | Stahl et al. |
| 6,469,061 B1 | 10/2002 | Flescher et al. |
| 6,482,943 B1 | 11/2002 | Blokhin et al. |
| 6,503,506 B1 | 1/2003 | Germano |
| 6,503,523 B2 | 1/2003 | Hoppe et al. |
| 6,506,915 B1 | 1/2003 | West |
| 6,511,800 B1 | 1/2003 | Singh |
| 6,531,117 B2 | 3/2003 | Heger et al. |

(Continued)

FOREIGN PATENT DOCUMENTS

| JP | S-57-75916 | 5/1982 |
|---|---|---|
| WO | WO-9316704 A1 | 9/1993 |

(Continued)

OTHER PUBLICATIONS

Bliznakov, E., "Effect of Stimulation of the Host Defense System by Coenzyme Q10 on Dibenzpyrene-Induced Tumors and Infection with Friend Leukemia Virus in Mice", Proc. Nat. Acad. Sci. USA, 70(2): 390-394 (Feb. 1973).
Bliznakov, E., et al., "Coenzymes Q: Stimulants of the Phagocytic Activity in Rats and Immune Response in Mice", Experientia, 26(9): 953-954 (Sep. 1970).
Crane FL (2000) New Functions for Coenzyme Q10, Protoplasm, 213:127-133.
Conklin KA (2004) Cancer Chemotherapy and Antioxidants, J.Nutr. 134:3201S-3204S.
de Oliveria (1998) A Nutritious Cocktail for the Treatment of Melanoma: A Case Report, Journal of Orthomolecular Medicine, 13(3).
Folkers, K., et al., "Survival of Cancer Patients on Therapy with Coenzyme Q10", Biochemical and Biophysical Research Communication, vol. 192: 241-245 (1993).

(Continued)

*Primary Examiner* — Jon P Weber
*Assistant Examiner* — Thane Underdahl
(74) *Attorney, Agent, or Firm* — McCarter & English, LLP; Elizabeth A. Hanley, Esq.; Jill A. Mello

(57) ABSTRACT

Topical formulations of CoQ10 reduce the rate of tumor growth in an animal subject. In the experiments described herein, CoQ10 was shown to increase the rate of apoptosis in a culture of skin cancer cells but not normal cells. Moreover, treatment of tumor-bearing animals with a topical formulation of CoQ10 was shown to dramatically reduce the rate of tumor growth in the animals.

19 Claims, 30 Drawing Sheets

(56) References Cited

U.S. PATENT DOCUMENTS

| | | |
|---|---|---|
| 6,569,463 B2 | 5/2003 | Patel et al. |
| 6,573,284 B1 | 6/2003 | Riley et al. |
| 6,576,660 B1 | 6/2003 | Liao et al. |
| 6,576,678 B1 | 6/2003 | Bruening et al. |
| 6,582,710 B2 | 6/2003 | Deckers et al. |
| 6,582,723 B2 | 6/2003 | Gorsek |
| 6,596,287 B2 | 7/2003 | Deckers et al. |
| 6,599,513 B2 | 7/2003 | Deckers et al. |
| 6,623,746 B1 | 9/2003 | Wadle et al. |
| 6,630,160 B1 | 10/2003 | Evans et al. |
| 6,632,443 B2 | 10/2003 | Borowy-Borowski et al. |
| 6,652,891 B2 | 11/2003 | Selzer |
| 6,682,763 B2 | 1/2004 | Kuno et al. |
| 6,686,485 B2 | 2/2004 | West |
| 6,696,484 B2 | 2/2004 | Liao et al. |
| 6,726,924 B2 | 4/2004 | Keller |
| 6,727,234 B2 | 4/2004 | Wiemer et al. |
| 6,733,790 B1 | 5/2004 | Garces Garces |
| 6,753,325 B2 | 6/2004 | Rosenbloom |
| 6,803,193 B1 | 10/2004 | Hopper et al. |
| 6,806,069 B2 | 10/2004 | Chokshi |
| 6,809,176 B2 | 10/2004 | Blokhin et al. |
| 6,866,864 B2 | 3/2005 | Mousa |
| 6,867,024 B2 | 3/2005 | Chokshi |
| 6,906,106 B2 | 6/2005 | Chevalier |
| 6,923,988 B2 | 8/2005 | Patel et al. |
| 7,005,274 B1 | 2/2006 | Terkeltaub et al. |
| 7,060,733 B2 | 6/2006 | Pandol et al. |
| 7,083,572 B2 | 8/2006 | Unger et al. |
| 7,083,780 B2 | 8/2006 | Ansmann et al. |
| 7,091,241 B2 | 8/2006 | Gilloteaux et al. |
| 7,101,536 B2 | 9/2006 | Mongiat et al. |
| 7,132,268 B2 | 11/2006 | Miyake et al. |
| 7,147,841 B2 | 12/2006 | Herzog |
| 7,169,385 B2 | 1/2007 | Fantuzzi et al. |
| 7,169,590 B2 | 1/2007 | Ueda et al. |
| 7,176,171 B2 | 2/2007 | Nieendick et al. |
| 7,179,880 B2 | 2/2007 | Kawa et al. |
| 7,182,938 B2 | 2/2007 | Andre et al. |
| 7,182,950 B2 | 2/2007 | Garti et al. |
| 7,198,801 B2 | 4/2007 | Carrara et al. |
| 7,208,298 B2 | 4/2007 | Miyake et al. |
| 7,247,714 B2 | 7/2007 | Kunsch et al. |
| 7,250,174 B2 | 7/2007 | Lee et al. |
| 7,268,107 B2 | 9/2007 | Nieendick et al. |
| 7,273,606 B2 | 9/2007 | Fantuzzi et al. |
| 7,279,456 B2 | 10/2007 | Dufay et al. |
| 7,311,897 B2 | 12/2007 | Ehlis et al. |
| 7,318,929 B2 | 1/2008 | Schieferstein et al. |
| 7,357,918 B2 | 4/2008 | Comte et al. |
| 7,456,161 B2 | 11/2008 | Nyce |
| 7,635,722 B1 | 12/2009 | Bachynsky et al. |
| 7,776,894 B2 | 8/2010 | Ronai et al. |
| 7,824,673 B2 | 11/2010 | Wegman et al. |
| 7,858,659 B2 | 12/2010 | Hoffman et al. |
| 7,879,823 B2 | 2/2011 | Seiberg et al. |
| 7,906,140 B2 | 3/2011 | Bromley et al. |
| 8,147,825 B2 | 4/2012 | Hsia et al. |
| 8,293,227 B2 | 10/2012 | Hsia et al. |
| 2001/0022965 A1 | 9/2001 | Heger et al. |
| 2001/0053356 A1 | 12/2001 | Mousa |
| 2002/0039595 A1 | 4/2002 | Keller |
| 2002/0044913 A1 | 4/2002 | Hamilton |
| 2002/0045230 A1 | 4/2002 | Rosen et al. |
| 2002/0048559 A1 | 4/2002 | Shinoda et al. |
| 2002/0048798 A1 | 4/2002 | Avery et al. |
| 2002/0049253 A1 | 4/2002 | Kaddurah-Daouk |
| 2002/0049422 A1 | 4/2002 | Brewitt |
| 2002/0058712 A1 | 5/2002 | Sneed |
| 2002/0071852 A1 | 6/2002 | Deckers et al. |
| 2002/0091288 A1 | 7/2002 | Wilbur et al. |
| 2002/0106337 A1 | 8/2002 | Deckers et al. |
| 2002/0114820 A1 | 8/2002 | Deckers et al. |
| 2002/0127252 A1 | 9/2002 | Kramer et al. |
| 2002/0136711 A1 | 9/2002 | Cochran |
| 2002/0146463 A1 | 10/2002 | Clayton |
| 2002/0155151 A1 | 10/2002 | Enzmann et al. |
| 2002/0156302 A1 | 10/2002 | West |
| 2002/0164317 A1 | 11/2002 | Gorsek |
| 2002/0182199 A1 | 12/2002 | Hoppe et al. |
| 2002/0198177 A1 | 12/2002 | Horrobin |
| 2003/0012762 A1 | 1/2003 | Zulli et al. |
| 2003/0012779 A1 | 1/2003 | Grieb et al. |
| 2003/0012825 A1 | 1/2003 | Kapper |
| 2003/0031688 A1 | 2/2003 | Ghosh et al. |
| 2003/0044441 A1 | 3/2003 | Schmid et al. |
| 2003/0077297 A1 | 4/2003 | Chen et al. |
| 2003/0087331 A1 | 5/2003 | Pettit et al. |
| 2003/0091518 A1 | 5/2003 | Pauly et al. |
| 2003/0103954 A1 | 6/2003 | Rosenbloom |
| 2003/0104048 A1 | 6/2003 | Patel et al. |
| 2003/0104080 A1 | 6/2003 | Singh et al. |
| 2003/0105027 A1 | 6/2003 | Rosenbloom |
| 2003/0105030 A1 | 6/2003 | Liao et al. |
| 2003/0105031 A1 | 6/2003 | Rosenbloom |
| 2003/0108493 A1 | 6/2003 | Henry et al. |
| 2003/0113354 A1 | 6/2003 | Schmid et al. |
| 2003/0118525 A1 | 6/2003 | Grigg |
| 2003/0118536 A1 | 6/2003 | Rosenbloom |
| 2003/0118576 A1 | 6/2003 | Brancato et al. |
| 2003/0124158 A1 | 7/2003 | Heidenfelder et al. |
| 2003/0129150 A1 | 7/2003 | Pauly et al. |
| 2003/0143166 A1 | 7/2003 | Heger et al. |
| 2003/0144346 A1 | 7/2003 | Liao et al. |
| 2003/0152598 A1 | 8/2003 | Heidenfelder et al. |
| 2003/0161849 A1 | 8/2003 | Heidenfelder et al. |
| 2003/0167556 A1 | 9/2003 | Kelley |
| 2003/0170265 A1 | 9/2003 | Henry et al. |
| 2003/0180231 A1 | 9/2003 | Danoux et al. |
| 2003/0180278 A1 | 9/2003 | Hoppe et al. |
| 2003/0180352 A1 | 9/2003 | Patel et al. |
| 2003/0185865 A1 | 10/2003 | Jentzsch et al. |
| 2003/0207834 A1 | 11/2003 | Dale et al. |
| 2003/0212114 A1 | 11/2003 | Sato |
| 2003/0215406 A1 | 11/2003 | Schreiner et al. |
| 2003/0219472 A1 | 11/2003 | Pauletti et al. |
| 2004/0028614 A1 | 2/2004 | Corbella et al. |
| 2004/0034107 A1 | 2/2004 | Enzmann |
| 2004/0043045 A1 | 3/2004 | Seipel et al. |
| 2004/0047896 A1 | 3/2004 | Malnoe et al. |
| 2004/0049022 A1 | 3/2004 | Nyce et al. |
| 2004/0063648 A1 | 4/2004 | Pandol et al. |
| 2004/0063661 A1 | 4/2004 | Linnane |
| 2004/0067260 A1 | 4/2004 | Milley et al. |
| 2004/0082522 A1 | 4/2004 | Nyce |
| 2004/0086538 A1 | 5/2004 | Sauermann et al. |
| 2004/0109880 A1 | 6/2004 | Pauly et al. |
| 2004/0110848 A1 | 6/2004 | Peffley et al. |
| 2004/0115181 A1 | 6/2004 | Fujii et al. |
| 2004/0122109 A1 | 6/2004 | Fujii et al. |
| 2004/0126367 A1 | 7/2004 | Fujii et al. |
| 2004/0142006 A1 | 7/2004 | Bleckmann et al. |
| 2004/0142007 A1 | 7/2004 | Moussou et al. |
| 2004/0142009 A1 | 7/2004 | Ansmann et al. |
| 2004/0151710 A1 | 8/2004 | Bozzacco |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0191263 A1 | 9/2004 | Hageman et al. |
| 2004/0197279 A1 | 10/2004 | Bleckmann et al. |
| 2004/0197354 A1 | 10/2004 | Doring et al. |
| 2004/0202740 A1 | 10/2004 | Tan |
| 2004/0219114 A1 | 11/2004 | Andersson et al. |
| 2004/0228910 A1 | 11/2004 | Enzmann et al. |
| 2004/0234559 A1 | 11/2004 | Bleckmann et al. |
| 2004/0253323 A1 | 12/2004 | Giles |
| 2004/0258717 A1 | 12/2004 | Sauermann et al. |
| 2005/0000390 A1 | 1/2005 | Nieendick et al. |
| 2005/0008581 A1 | 1/2005 | Parkhideh |
| 2005/0019268 A1 | 1/2005 | Enzmann |
| 2005/0019278 A1 | 1/2005 | Berg-Schultz |
| 2005/0019353 A1 | 1/2005 | Prinz et al. |
| 2005/0025756 A1 | 2/2005 | Erwin |
| 2005/0026848 A1 | 2/2005 | Robinson et al. |

(56) References Cited

U.S. PATENT DOCUMENTS

| | | |
|---|---|---|
| 2005/0026850 A1 | 2/2005 | Robinson et al. |
| 2005/0036976 A1 | 2/2005 | Rubin et al. |
| 2005/0037036 A1 | 2/2005 | Nielsen et al. |
| 2005/0037102 A1 | 2/2005 | Tan et al. |
| 2005/0043336 A1 | 2/2005 | Hennequin et al. |
| 2005/0058610 A1 | 3/2005 | Baschong et al. |
| 2005/0069582 A1 | 3/2005 | Fantuzzi |
| 2005/0070610 A1 | 3/2005 | Fujii et al. |
| 2005/0070611 A1 | 3/2005 | Fantuzzi |
| 2005/0079164 A1 | 4/2005 | Fantuzzi et al. |
| 2005/0100537 A1 | 5/2005 | Evans et al. |
| 2005/0106190 A1 | 5/2005 | Kawa et al. |
| 2005/0106199 A1 | 5/2005 | Schreiber et al. |
| 2005/0112156 A1 | 5/2005 | Busch et al. |
| 2005/0118209 A1 | 6/2005 | Jentszch et al. |
| 2005/0136081 A1 | 6/2005 | Kawa et al. |
| 2005/0142123 A1 | 6/2005 | Chen et al. |
| 2005/0142153 A1 | 6/2005 | Schreiber et al. |
| 2005/0147598 A1 | 7/2005 | Ueda et al. |
| 2005/0148603 A1 | 7/2005 | Jimenez et al. |
| 2005/0152856 A2 | 7/2005 | Andersson et al. |
| 2005/0184275 A1 | 8/2005 | Mora-Gutierrez et al. |
| 2005/0202521 A1 | 9/2005 | Crum |
| 2005/0214333 A1 | 9/2005 | Lanzendoerfer et al. |
| 2005/0220726 A1 | 10/2005 | Pauly et al. |
| 2005/0220826 A1 | 10/2005 | Kawa et al. |
| 2005/0226824 A1 | 10/2005 | Kawa et al. |
| 2005/0226858 A1 | 10/2005 | Kitamura et al. |
| 2005/0226947 A1 | 10/2005 | Kern |
| 2005/0238679 A1 | 10/2005 | Biergiesser et al. |
| 2005/0239721 A1 | 10/2005 | Rosenbloom |
| 2005/0255057 A1 | 11/2005 | Andre et al. |
| 2005/0276764 A1 | 12/2005 | Kolbe et al. |
| 2005/0281772 A1 | 12/2005 | Bromley et al. |
| 2005/0287206 A1 | 12/2005 | Fantuzzi et al. |
| 2005/0288333 A1 | 12/2005 | Kem |
| 2006/0002964 A9 | 1/2006 | Schreiber et al. |
| 2006/0008482 A1 | 1/2006 | Prinz et al. |
| 2006/0010519 A1 | 1/2006 | Kadowaki et al. |
| 2006/0013888 A1 | 1/2006 | Fantuzzi |
| 2006/0035981 A1 | 2/2006 | Mazzio et al. |
| 2006/0039956 A1 | 2/2006 | Hensen et al. |
| 2006/0041017 A1 | 2/2006 | Chopra |
| 2006/0051462 A1 | 3/2006 | Wang |
| 2006/0052438 A1 | 3/2006 | Ho et al. |
| 2006/0062755 A1 | 3/2006 | Woodward |
| 2006/0069068 A1 | 3/2006 | Kajander et al. |
| 2006/0073106 A1 | 4/2006 | Berg-Schultz et al. |
| 2006/0093633 A1 | 5/2006 | Stab et al. |
| 2006/0099158 A1 | 5/2006 | Zander et al. |
| 2006/0099244 A1 | 5/2006 | Guilford |
| 2006/0110415 A1 | 5/2006 | Gupta |
| 2006/0120997 A1 | 6/2006 | Lipton |
| 2006/0121016 A1 | 6/2006 | Lee |
| 2006/0127384 A1 | 6/2006 | Capaccioli et al. |
| 2006/0128643 A1 | 6/2006 | Kaddurah-Daouk et al. |
| 2006/0153783 A1 | 7/2006 | Ehlis et al. |
| 2006/0188459 A1 | 8/2006 | Heinrichs et al. |
| 2006/0188492 A1 | 8/2006 | Richardson et al. |
| 2006/0193905 A1 | 8/2006 | Ehringer et al. |
| 2006/0205771 A1 | 9/2006 | Noble et al. |
| 2006/0251690 A1 | 11/2006 | Lipshutz et al. |
| 2006/0251708 A1 | 11/2006 | Chen et al. |
| 2006/0286046 A1 | 12/2006 | Haber |
| 2006/0292220 A1 | 12/2006 | Giordano et al. |
| 2007/0021360 A1 | 1/2007 | Nyce et al. |
| 2007/0026072 A1 | 2/2007 | Olsen et al. |
| 2007/0053985 A1 | 3/2007 | Ueda et al. |
| 2007/0071779 A1 | 3/2007 | McKie |
| 2007/0085059 A1 | 4/2007 | Mora-Gutierrez et al. |
| 2007/0092469 A1 | 4/2007 | Jacobs |
| 2007/0104701 A1 | 5/2007 | Ueda et al. |
| 2007/0104810 A1 | 5/2007 | Kern |
| 2007/0110731 A1 | 5/2007 | Riley |
| 2007/0129428 A1 | 6/2007 | Richelle et al. |
| 2007/0149618 A1 | 6/2007 | Cuevas Sanchez et al. |
| 2007/0172436 A1 | 7/2007 | Zhang |
| 2007/0184041 A1 | 8/2007 | Burja |
| 2007/0184076 A1 | 8/2007 | Unger et al. |
| 2007/0189994 A1 | 8/2007 | Berg et al. |
| 2007/0196349 A1 | 8/2007 | Kitamura et al. |
| 2007/0196914 A1 | 8/2007 | Murray et al. |
| 2007/0202090 A1 | 8/2007 | Prosek et al. |
| 2007/0218042 A1 | 9/2007 | Khaled |
| 2007/0225255 A1 | 9/2007 | Frohlich et al. |
| 2007/0243180 A1 | 10/2007 | Tanaka et al. |
| 2007/0248590 A1 | 10/2007 | Milne et al. |
| 2007/0248693 A1 | 10/2007 | Mazzio et al. |
| 2007/0253941 A1 | 11/2007 | Naidu et al. |
| 2007/0258966 A1 | 11/2007 | Ueda et al. |
| 2007/0258967 A1 | 11/2007 | Ueda et al. |
| 2007/0275021 A1 | 11/2007 | Lee et al. |
| 2008/0020018 A1 | 1/2008 | Moodley et al. |
| 2008/0020022 A1 | 1/2008 | Udell |
| 2008/0025929 A1 | 1/2008 | Burton et al. |
| 2008/0031862 A1 | 2/2008 | Ghosal |
| 2008/0057116 A1 | 3/2008 | Pleva |
| 2008/0063674 A1 | 3/2008 | Vollhardt et al. |
| 2008/0069779 A1 | 3/2008 | Tamarkin et al. |
| 2008/0069898 A1 | 3/2008 | Smith et al. |
| 2008/0075684 A1 | 3/2008 | Barg et al. |
| 2008/0081034 A1 | 4/2008 | Zimmerman et al. |
| 2008/0081082 A1 | 4/2008 | Zimmerman et al. |
| 2008/0089852 A1 | 4/2008 | Hotz et al. |
| 2008/0089913 A1 | 4/2008 | Kallmayer et al. |
| 2008/0095719 A1 | 4/2008 | Herrmann et al. |
| 2008/0102313 A1 | 5/2008 | Nilsen et al. |
| 2008/0260878 A1 | 10/2008 | Harano et al. |
| 2008/0287541 A1 | 11/2008 | Hoffman et al. |
| 2009/0010917 A1 | 1/2009 | Rosenblum et al. |
| 2009/0137556 A1 | 5/2009 | Bonnichsen |

FOREIGN PATENT DOCUMENTS

| | | |
|---|---|---|
| WO | WO-9505164 | 2/1995 |
| WO | WO-9617626 A2 | 6/1996 |
| WO | WO-9835660 A1 | 8/1998 |
| WO | WO-9911242 A1 | 3/1999 |
| WO | WO-0007607 A1 | 2/2000 |
| WO | WO-02062329 A1 | 8/2002 |
| WO | WO-02078727 A1 | 10/2002 |
| WO | WO-02085297 A2 | 10/2002 |
| WO | WO-03008405 A1 | 1/2003 |
| WO | WO-2004003564 A2 | 1/2004 |
| WO | WO-2006017494 A2 | 2/2006 |
| WO | WO-2006063402 A1 | 6/2006 |

OTHER PUBLICATIONS

Hodges, et al., "CoQ10: could it have a role in cancer management?", BioFactors, vol. 9, pp. 365-370 (1999).

Kawase I (1978) Enhancing Effect of Coenzyme Q10 on Immunorestoration with Mycobacterium bovia BCG in Tumor-Bearing Mice Gann, 69(4):493-497.

Kokawa, T., et al., "Coenzyme Q10 in cancer chemotherapy—experimental studies on augmentation of the effects of masked compounds, especially in the combined chemotherapy with immunopotentiators", XP002473825 Database accession No. NLM6881995(Abstract) (Mar. 1983).

Lamson et al. "Antioxidants in Cancer Therapy; Their Actions and Interactions With Oncologic Therapies" Alternative Medicine Review, vol. 4, No. 5, 1999, pp. 304-329.

Larsson O (1994) Effets of Isoprenoids on Growth of Normal Human Mammary Epithelial Cells and Breast Cancer Cells in vitro. Anticancer Research 14:123-128.

Li, GJ (1987) Protective Effect of Coenzyme Q10 against the Adverse Reaction of Mytomycin G in Mouse Liver Acta Histochemica et Cytochemica 1087, 20(4):455-467.

Lockwood, et al., "Apparent partial remission of breast cancer in 'high risk' patients supplemented with nutritional antioxidants, essential fatty acids and coenzyme Q10", Mol-Aspects-Med., vol. 15 Suppl. pp. 231-240 (1994) (Abstract Only).

(56) References Cited

OTHER PUBLICATIONS

Lockwood, et al., "Partial and complete regression of breast cancer in patients in relation to dosage of coenzyme Q10", Biochem-Biophys-Res-Commun., 199(3), pp. 1504-1508 (1994) (Abstract Only).

Lockwood, et al., "Progress on Therapy of Breast Cancer with Vitamin Q10 and the Regression of Metastases", Biochem-Biophys-Res-Commun 212(1) pp. 172-177 (1995).

Palan PR et al (2003) Plasma Concentrations of Coenzyme Q10 and Tocopherols in Cervical Intraepithelial Neoplasia and Cervical Cancer. Eur. J. Cancer Prev. 12:321-326.

Roffe et al (2004) Efficacy of Coenzyme Q10 for Improved Tolerability of Cancer Treatments: A Systematic Review. J. Clin. Oncol. 22:4418-24.

Shekelle P, et al. (2003) Effect of the Supplemental Use of Antioxidants Vitamin C, Vitamin E, and Coenzyme Q10 for the Prevention and Treatment of Cancer. Evid. Rep. Technol. Assess. 75:1-3.

Shimizu T (2003) Paclitaxel Pirarubicin Weekly. Japan J. Cancer and Chemotherapy 30:105-109.

The National Cancer Institute, "Coenzyme Q10 (PDQ.RTM.) Patient Version", http://www.cancer.gov/cancertopics/pdq/cam/coenzymeQ10/patient/allpages; Jul. 10, 2009.

Seifried, et al., the antioxidant conundrum in cancer. Cancer Res. 2003, 63(15):4295-8.

Women's Health Update: Coenzyme Q10 and Breast Cancer, http://www.encognitive.com/node/13574, Dec. 26, 2012, 4pgs.

In Vitro Study of SK MEL Cells in Medium containing Coenzyme Q10 After 48 Hour Incubation Control 0 μM CoQ10    20 μM CoQ10    100 μM CoQ10

The Effect of Coenzyme Q10 Vehicle on Human Melanoma cell line SKMEL28

After 48hr Incubation
* Significant compared to Ctrl   P<0.05

■ Control
▨ Treatment

The Effect of Rx The Effect of Coenzyme Q10 on Human Breast Adenocarcinoma MCF-7 Cell line After 72hr Incubation
*Significant compared to Ctrl  P<0.05*

Appearance of Tumors on Treatment Mouse Vs. Control Mouse

Mice Before Excision of Tumors

In Vitro Study of Human Breast Adenocarcinoma Cell Line SK-BR-3 Incubated in Medium Supplemented with Coenzyme Q10 for a 72 Hour Period The Effect of Coenzyme Q10 on Breast Cancer BT-20 Cell Line

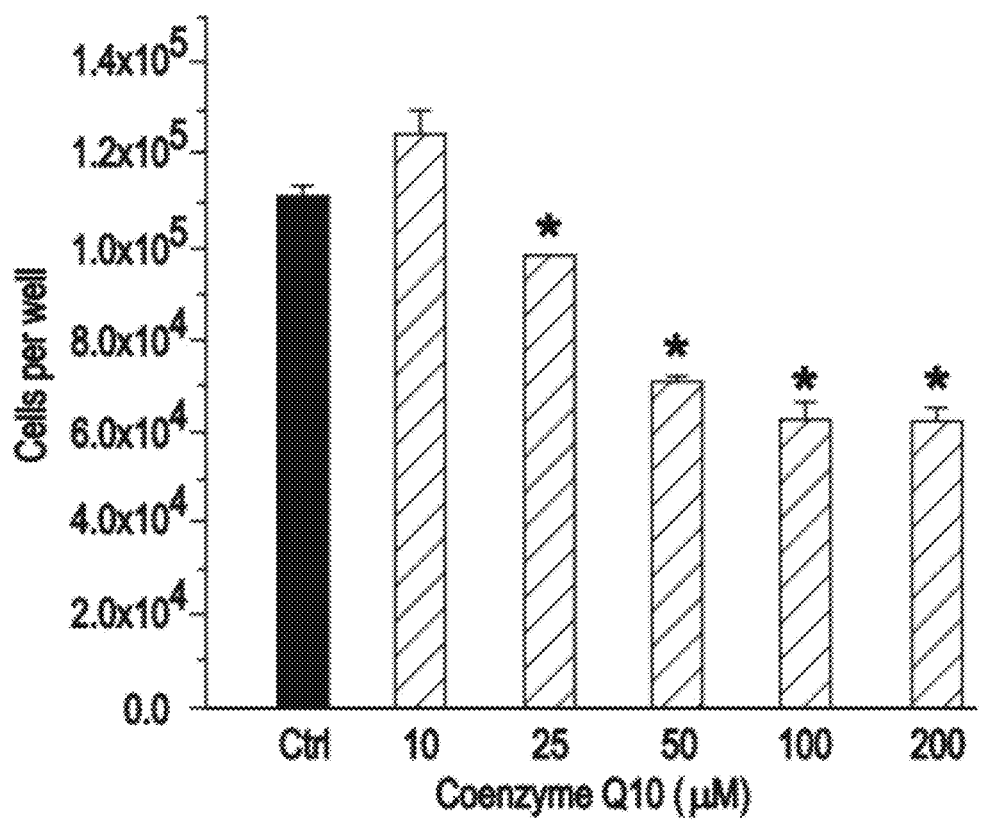

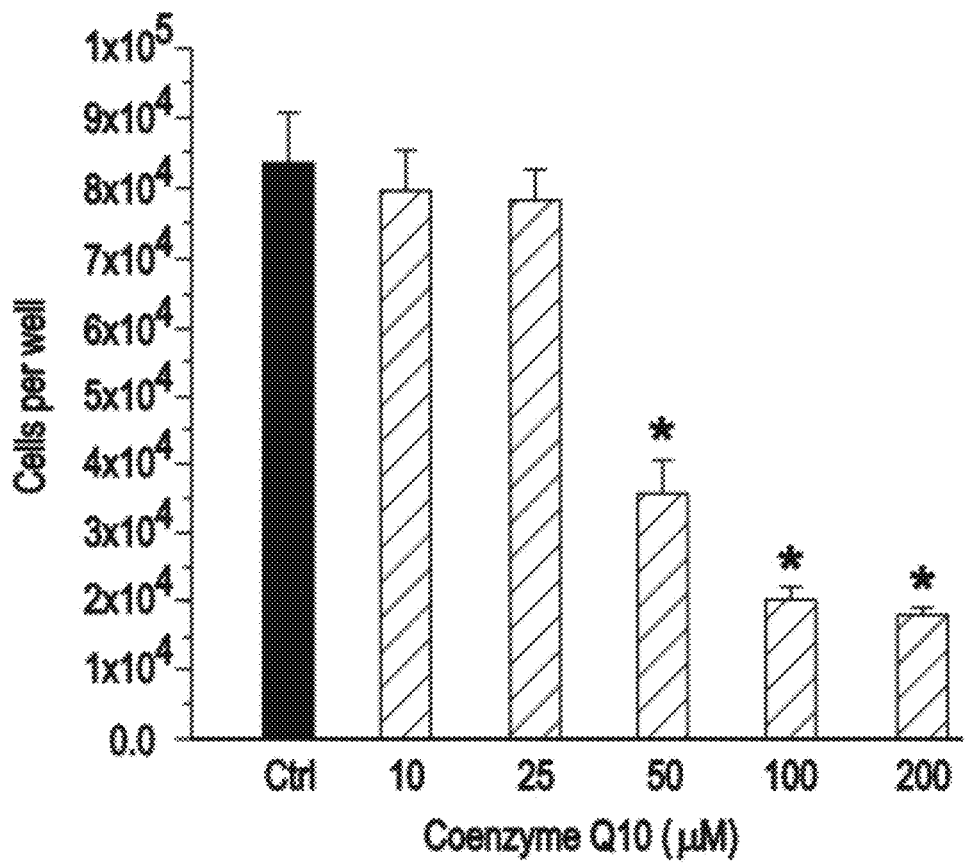

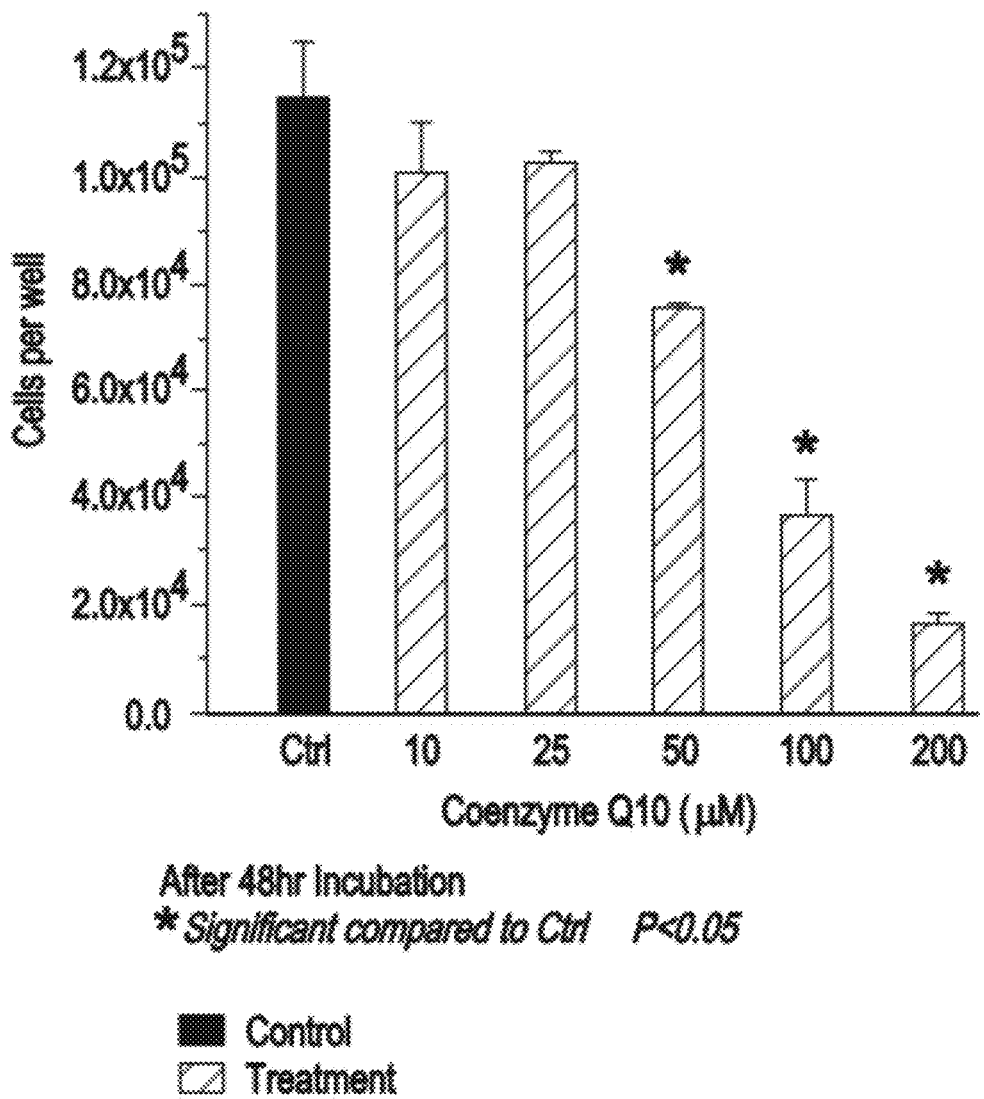

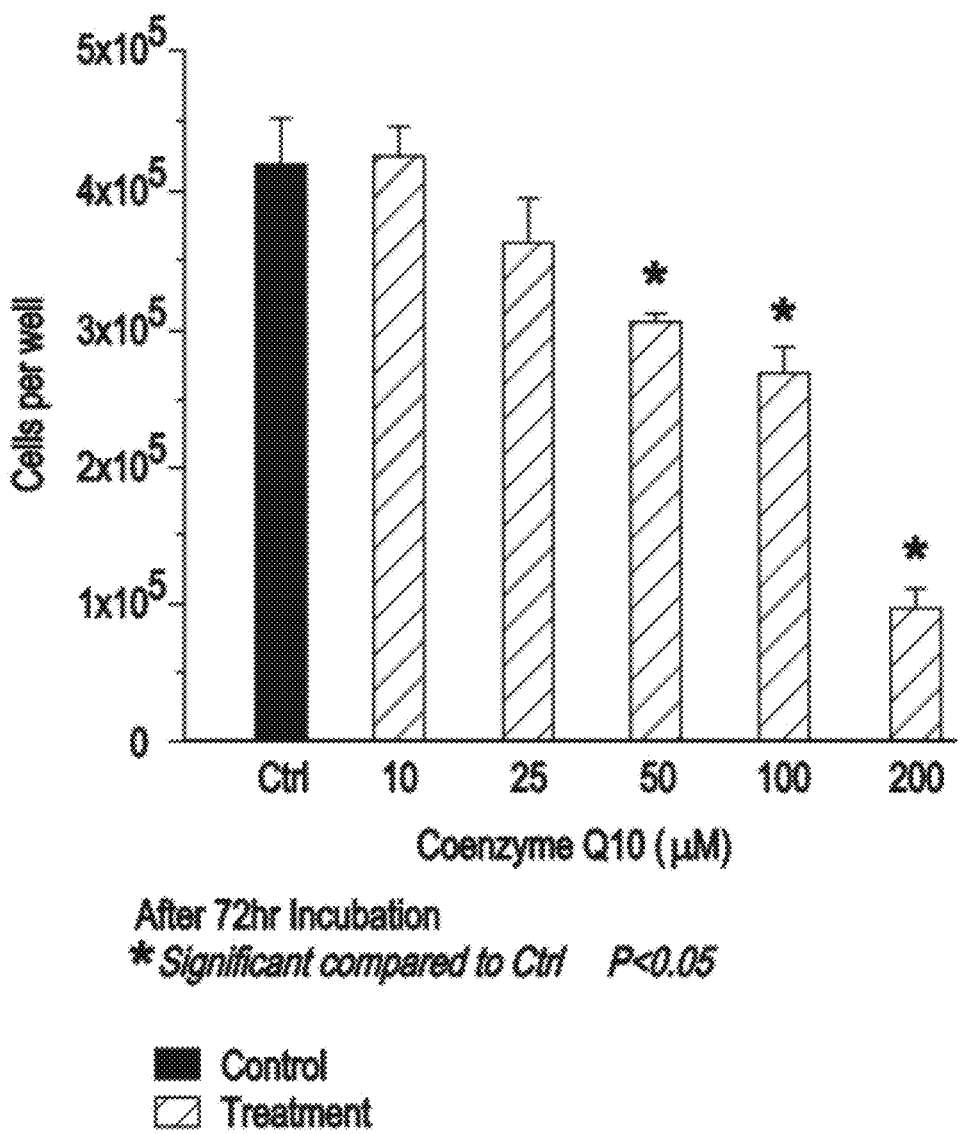

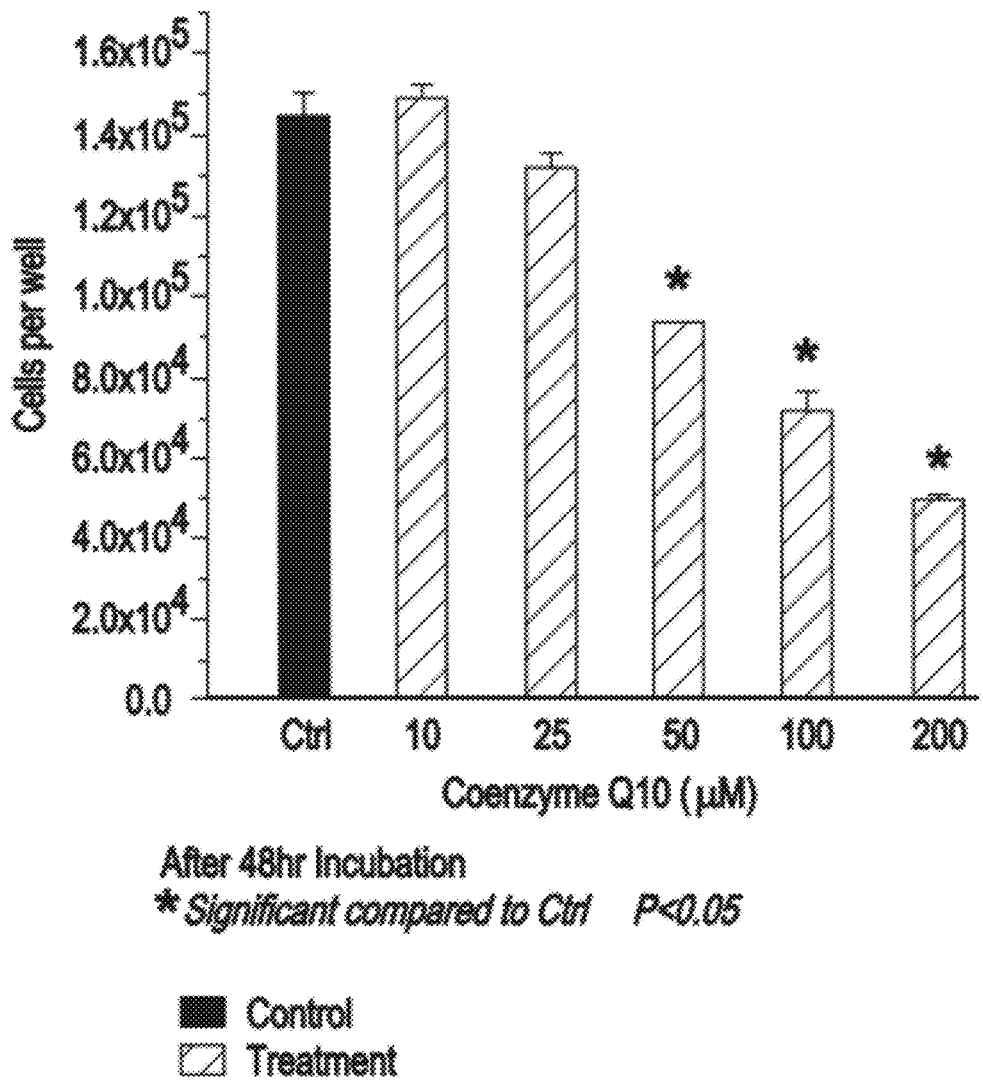

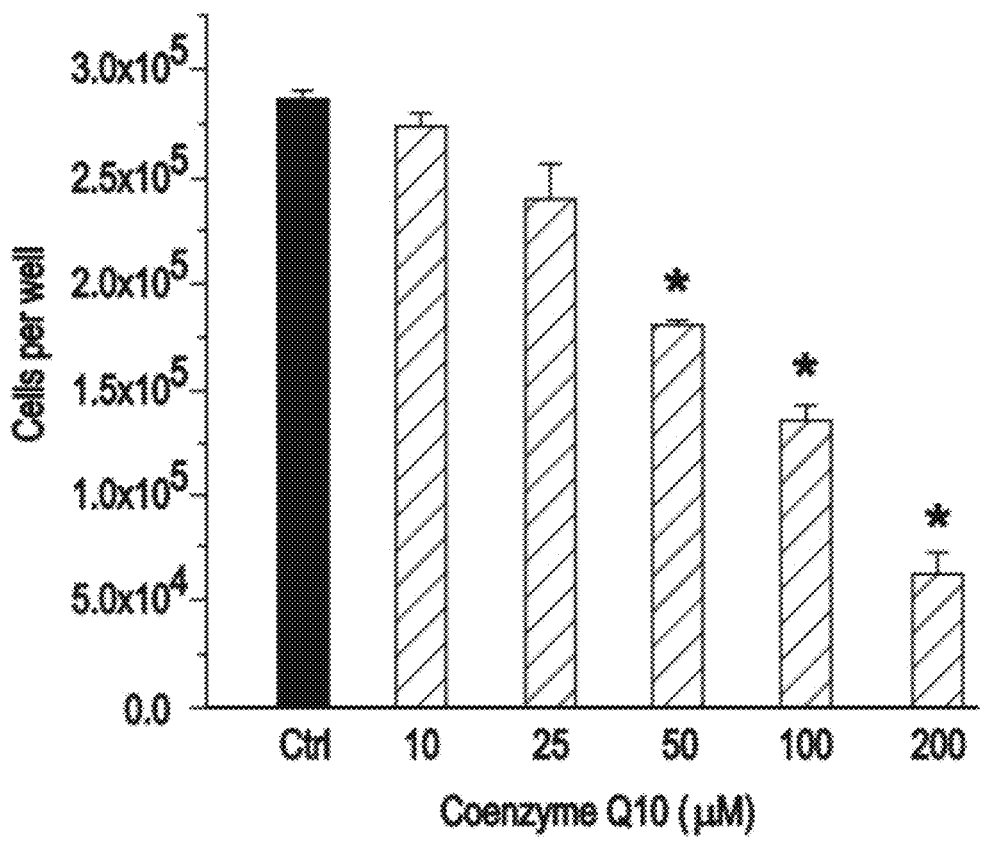

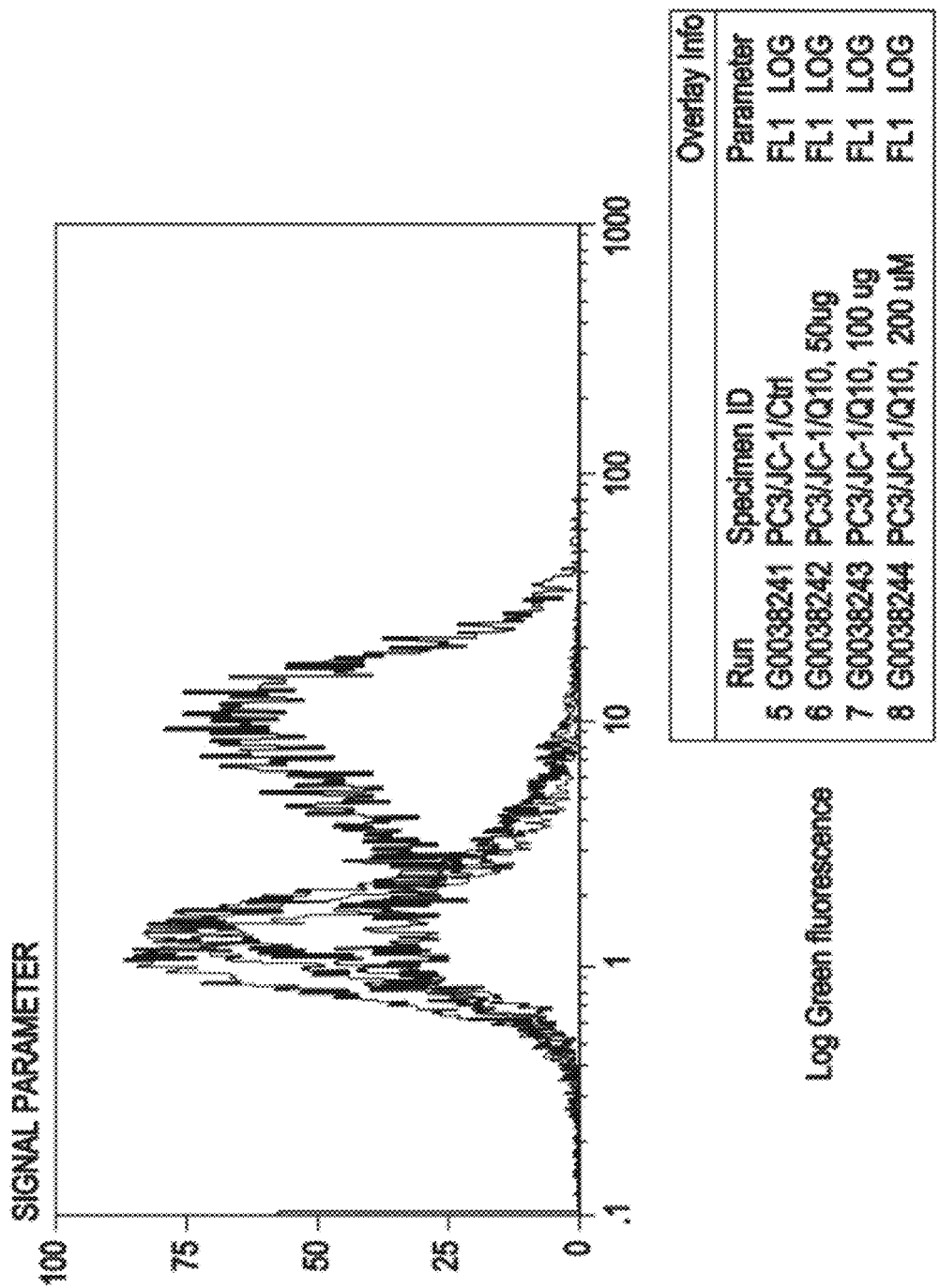

CO-ENZYME Q10 FORMULATIONS AND METHODS OF USE

FIELD OF THE INVENTION

The invention provides pharmaceutical compositions comprising co-enzyme Q10 (CoQ10) and methods of using CoQ10 for treatment of cancer, selective reduction of cancer cell growth, induction of apoptosis in cancer cells and inhibition of tumor mediated angiogenesis.

BACKGROUND

Cancer is presently one of the leading causes of death in developed nations. Although recent research has vastly increased our understanding of many of the molecular mechanisms of tumorigenesis and has provided numerous new avenues for the treatment of cancer, standard treatments for most malignancies remain gross resection, chemotherapy, and radiotherapy. While increasingly successful, each of these treatments still causes numerous undesired side effects. For example, surgery results in pain, traumatic injury to healthy tissue, and scarring. Radiotherapy and chemotherapy cause nausea, immune suppression, gastric ulceration and secondary tumorigenesis.

SUMMARY

The invention relates to the discovery that topical formulations of CoQ10 can reduce the rate of tumor growth in an animal subject. In the experiments described herein, CoQ10 was shown to increase the rate of apoptosis in a culture of skin cancer cells but not normal cells. Moreover, treatment of tumor-bearing animals with a topical formulation of CoQ10 was shown to dramatically reduce the rate of tumor growth in the animals.

CoQ10 formulated for oral delivery has previously been used as a dietary supplement. Orally administered CoQ10 has, however, been shown to accumulate in the liver-diminishing its systemic availability. The anti-tumor responses observed with topically applied CoQ10 may relate to its higher bioavailability compared to dietary supplement forms of the CoQ10.

Accordingly, the invention features a method for reducing the rate of tumor cell growth or increasing the rate of apoptosis in tumor cells in a subject. The method includes the steps of providing a subject having a plurality of tumor cells and administering to the subject a composition comprising an effective amount of CoQ10 and a pharmaceutically acceptable carrier.

In another aspect, the invention features a composition comprising an effective amount of CoQ10 and a pharmaceutically acceptable carrier.

In a preferred embodiment, the composition is a topical formulation of CoQ10 that includes at least about 0.01% by weight CoQ10 up to 30% by weight (w/w) of CoQ10 and a carrier suitable for delivering the CoQ10 topically. Preferably, the pharmaceutical composition comprises as an active ingredient CoQ10 and a pharmaceutically acceptable carrier. The composition comprising, Coenzyme Q10, phospholipon 90, glycerol, butylated hydroxytoluene (BHT), ethanol, medium chain triglycerides (MCT) and lavender. Preferably, the phospholipon 90 is phospholipon 90G and/or phospholipon 90H.

In a preferred embodiment, the pharmaceutical composition comprises at least about 0.01% to about 30% (w/w) of Coenzyme Q10. Preferably, the pharmaceutical composition between about 1% to about 25% (w/w) of Coenzyme Q10.

In another preferred embodiment, the invention provides a method of treating a cancer patient, comprising:
administering to a patient in need thereof, a composition comprising a therapeutically effective amount of Coenzyme Q10;
contacting a tumor cell with the composition resulting in the lysis of the tumor cell; thereby treating the cancer patient.

Preferably, the pharmaceutical composition comprises at least about 0.01% up to 30% w/w of Coenzyme Q10, preferably, the pharmaceutical composition comprises about 1% to about 25% w/w of Coenzyme Q10.

In another preferred embodiment, the pharmaceutical composition is formulated in a topical cream with optional transdermal enhancers.

In other preferred embodiments, a therapeutically effective amount of the Coenzyme Q10 composition is administered with one or more chemotherapeutic agents. These chemotherapeutic agents can be co-administered, precede, or administered after the Coenzyme Q10. Non-limiting examples of chemotherapeutic agents include, but not limited to: cyclophosphamide (CTX, 25 mg/kg/day, p.o), taxanes (paclitaxel or docetaxel), busulfan, cisplatin, cyclophosphamide, methotrexate, daunorubicin, doxorubicin, melphalan, cladribine, vincristine, vinblastine, and chlorambucil.

In another preferred embodiment, the pharmaceutical composition, Coenzyme Q10 composition inhibits the tumor cell growth in a subject, and the method comprises administering to the subject a pharmaceutical composition comprising a therapeutically effective amount of CoQ10. Preferably, the therapeutically effective amount of Coenzyme Q10 in the pharmaceutical composition comprises between about 0.01% and 30% w/w of coenzyme Q10 Inhibition of tumor cell growth refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

In another preferred embodiment, the invention provides a method of inducing apoptosis selectively in a tumor cell, the method comprising administering a pharmaceutical composition comprising coenzyme Q10 as measured in standard assays. Preferably, the pharmaceutical composition comprises at least about 0.01% up to 30% w/w of Coenzyme Q10. Methods for measuring apoptosis include but not limited to mitochondrial membrane dye assays and/or Annexin-VPE assays. In a preferred embodiment, the pharmaceutical composition induces apoptosis in at least about 30% of tumor cells as measured by mitochondrial membrane dye assay and/or Annexin-VPE assay. Preferably, the pharmaceutical composition induces apoptosis in about 60% of tumor cells as measured by mitochondrial membrane dye assay and/or Annexin-VPE assay, more preferably, the pharmaceutical composition induces apoptosis in about 75% of tumor cells as measured by mitochondrial membrane dye assay and/or Annexin-VPE assay, more preferably, the pharmaceutical composition induces apoptosis in about 90%, 91%, 92%, 93%, 94%, 95%, 96%, 97%, 98%, 99% and 100% of rumor cells as measured by mitochondrial membrane dye assay and/or Annexin-VPE assay.

In another preferred embodiment, the invention provides a method of inhibiting angiogenesis in a tumor, the method comprising contacting a tumor with a pharmaceutical composition comprising coenzyme Q10. Preferably, the pharmaceutical composition comprises at least about 0.01% up to 30% w/w of Coenzyme Q10.

Additional uses for the present compounds include use in the treatment of atherosclerosis, inflammation, and as an anti-angiogenic agent, especially to treat cancers, particularly solid cancers such as cancers residing in the lung, breast, liver, brain or other tissue.

Unless otherwise defined, all technical terms used herein have the same meanings as commonly understood by one of ordinary skill in the art to which this invention belongs. Commonly understood definitions of medical terms can be found in Thomas Lathrop Stedman, Stedman's Medical Dictionary, Lippincott, Williams & Wilkins: Philadelphia, Pa., 2000.

All publications, patent applications, patents and other references mentioned herein are incorporated by reference in their entirety. In the case of conflict, the present specification, including definitions will control. The particular embodiments discussed below are illustrative only and not intended to be limiting.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 22 is a graph showing that CoQ10 reduces the proliferation of a human hepatocellular carcinoma cell line (Hep 3B) in a 48 hour in vitro culture.

FIG. 23 is a graph showing that CoQ10 reduces the proliferation of a human hepatocellular carcinoma cell line (Hep 3B) in a 72 hour in vitro culture.

FIG. 24 is a graph showing that CoQ10 reduces the proliferation of a human osteosarcoma cell line (143B) in a 48 hour in vitro culture.

FIG. 25 is a graph showing that CoQ10 reduces the proliferation of a human osteosarcoma cell line (143B) in a 72 hour in vitro culture.

FIG. 26 is a graph showing that CoQ10 reduces the proliferation of a human prostatic adenocarcinoma cell line (PC-3) in a 48 hour in vitro culture.

FIG. 27 is a graph showing that CoQ10 reduces the proliferation of a human prostatic adenocarcinoma cell line (PC-3) in a 72 hour in vitro culture.

FIG. 28 is a graph showing the effect of CoQ10 on mitochondrial polarization (an indicator of apoptosis) of a human prostatic adenocarcinoma cell line (PC-3) in a 24 hour in vitro culture. PC-3 cell cultures were treated with Q10 at 0.05, 0.1 and 0.2 mM concentrations for 24 h and then treated with JC-1, at 10 microgram/ml., for 30 min. Uptake and levels of green fluorescence was measured in a flow cytometer, FL1

(green fluor.). Note: A significant increase in the green fluorescence was observed in 0.2 mM Q10 treated cells (yellow graph).

Figure 29A:
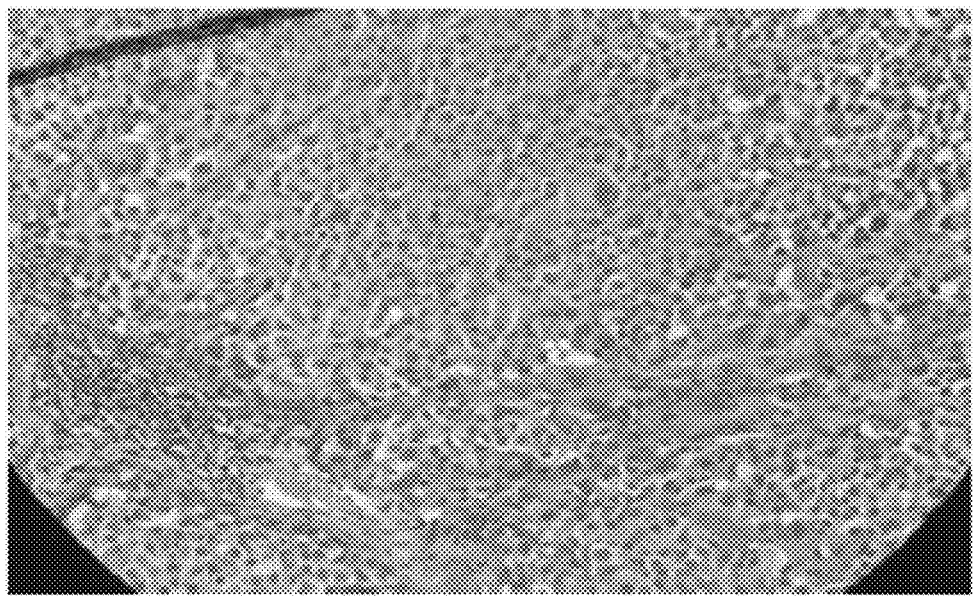
Figure 29B:
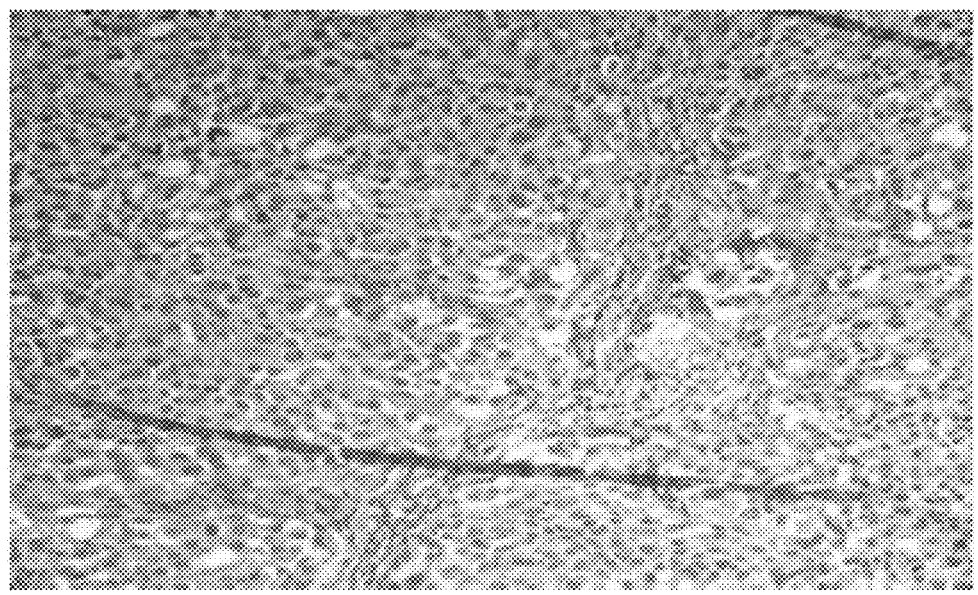

FIGS. 29A and 29B are photographs showing inhibition of tumor-mediated angiogenesis in tissues by a composition comprising CoQ10 (FIG. 29B) as compared to a control in the absence of a composition comprising CoQ10.

DETAILED DESCRIPTION

The invention provides compositions and methods for reducing the rate of tumor cell growth or increasing the rate of tumor cell apoptosis. Compositions of the invention include as an anti-tumor agent a therapeutically effective amount of CoQ10 and a carrier. A preferred composition of the invention is a topical formulation of CoQ10 comprising at least about 1% CoQ10 and a carrier that facilitates topical delivery of CoQ10. A most preferred composition of the invention is a topical formulation of CoQ10 comprising between about 1% and 15% CoQ10 and a carrier that facilitates topical delivery of CoQ10. Methods of the invention for killing a tumor cell or reducing its growth rate include the step of contacting the cell with an effective concentration of CoQ10.

The below described preferred embodiments illustrate adaptations of these compositions and methods. Nonetheless, from the description of these embodiments, other aspects of the invention can be made and/or practiced based on the description provided below.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

DEFINITIONS

In accordance with the present invention and as used herein, the following terms are defined with the following meanings, unless explicitly stated otherwise.

As used herein, "a", "an," and "the" include plural references unless the context clearly dictates otherwise.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and therapeutic effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

As used herein, "cancer" refers to all types of cancer or neoplasm or malignant tumors found in mammals, including, but not limited to: leukemias, lymphomas, melanomas, carcinomas and sarcomas. In preferred embodiments, the CoQ10 compositions are used for treatment, of various types of breast cancer; prostate cancer; liver cancer; bone cancer. However, treatment using the CoQ10 compositions are not limited to these types of cancers.

Examples of cancers are cancer of the brain, breast, pancreas, cervix, colon, head and neck, kidney, lung, non-small cell lung, melanoma, mesothelioma, ovary, sarcoma, stomach, uterus and Medulloblastoma. As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

The term "sarcoma" generally refers to a. tumor which is made up of a substance like the embryonic connective tissue and is generally composed of closely packed cells embedded in a fibrillar or homogeneous substance. Examples of sarcomas which can be treated with the present compositions and optionally a potentiator and/or chemotherapeutic agent include, but not limited to a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the compositions of the invention and optionally a potentiator and/or another chemotherapeutic agent include but not limited to, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the compositions of the invention and optionally a potentiator and/or a chemotherapeutic agent include but not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Additional cancers which can be treated with the compositions of the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests. For example, the "treatment of cancer" or "tumor cells", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

A "chemokine" is a small cytokine involved in the migration and activation of cells, including phagocytes and lymphocytes, and plays a role in inflammatory responses.

A "cytokine" is a protein made by a cell that affect the behavior of other cells through a "cytokine receptor" on the surface of the cells the cytokine effects. Cytokines manufactured by lymphocytes are sometimes termed "lymphokines." Cytokines are also characterized as Type I (e.g. IL-2 and IFN-γ) and Type II (e.g. IL-4 and IL-10).

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values.

As used herein, the term "selective for tumor cells" refers to the effects of the Coenzyme Q10 pharmaceutical compositions, such as inhibition of tumor growth, apoptosis, anti-angiogenic effects and which are not detectable when applied to normal cells, as described in detail in the examples which follow.

CoQ10 Compositions

In a preferred embodiment, the invention provides CoQ10 compositions for the treatment of cancer. Preferably, the compositions comprise at least about 1% to about 25% CoQ10 w/w, more preferably, between about 1% to about 20% CoQ10 w/w. In the representative embodiment described in the Examples section below, a topical formulation of CoQ10 is applied to the skin of a tumor-bearing animal to reduce the growth rate of the tumor. CoQ10 can be obtained from Pure Prescriptions (San Diego, Calif.) in powdered form in any suitable quantity (e.g., 1 kilogram). To deliver a CoQ10-containing composition, any suitable carrier can be used. Liposomes, for example, may be used as a carrier. An exemplary liposomal formulation is composed of Phospholipon 90G (American Lechitin, Stanford, Conn.), Phospholipon 90H (American Lechitin, Stanford, Conn.), Glycerol, Butylated hydroxytoluene (BHT), Ethanol, Medium Chain Triglycerides (MCT), lavender (Sigma-Aldrich, St. Louis, Mo.) and Coenzyme Q10 (Pure Prescriptions, San Diego, Calif.). An example of a protocol for preparing this formulation entails first dissolving 10 g of Phospholipon 90H, 5 g Phospholipon 90G, with 1.5 g MCT, 0.3 g BHT, and 9 ml of ethanol at 75° C. Next, 1.1 g of Coenzyme Q10 are dissolved into the mixture. 65 ml of 1 mM phosphate buffer (pH 8.2) prepared with nitrogen saturated water, 13.3 g glycerol, and 50 μL of lavender are added. The above mixture is blended in a high-speed blender at 12,000 RPM to form a cream. The cream is stored at 4° C. until used.

Subjects

Because subjects from many different species have tumors and are susceptible to acquiring a tumor, the invention is compatible with many types of animal subjects. A non-exhaustive exemplary list of such animals includes mammals such as mice, rats, rabbits, goats, sheep, pigs, horses, cattle, dogs, cats, and primates such as monkeys, apes, and human beings. Those animal subjects known to suffer from a skin cancer tumor are preferred for use in the invention. In particular, human patients suffering from a skin cancer tumor or other tumors are suitable animal subjects for use in the invention. By adapting the methods taught herein to other methods known in medicine or veterinary science (e.g., adjusting doses of administered substances according to the weight of the subject animal), the compositions utilized in the invention can be readily optimized for use in other animals.

Pharmaceutical Compositions and Administration to a Subject

In a preferred embodiment, the compositions comprising CoQ10 are administered topically. It is preferable to present the active ingredient, i.e. CoQ10 as a pharmaceutical formulation. Exemplary compositions are described in detail in the examples which follow. The active ingredient may comprise, for topical administration, from 0.001% to about 20% w/w, by weight of the formulation in the final product., although it may comprise as much as 30% w/w, preferably from about 1% to about 20% w/w of the formulation. The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

The composition of the invention can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. In addition to treatment of cancer with topical formulations of CoQ10, in other aspects of the invention CoQ10 might be delivered by other methods. For example, CoQ10 might be formulated for parenteral delivery, e.g., for subcutaneous, intravenous, intramuscular, or intratumoral injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions are preferably formulated in a sterilized pyrogen-free form. Compositions of the invention can also be administered in vitro to a cell (for example, to induce apoptosis in a cancer cell in an in vitro culture) by simply adding the composition to the fluid in which the cell is contained.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. See, for example, FIG. 14. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate is a preferred buffer.

The final pH value of the pharmaceutical composition may vary within the physiological compatible range. Necessarily, the final pH value is one not irritating to human skin and preferably such that transdermal transport of the active compound, i.e. CoQ10 is facilitated. Without violating this constraint, the pH may be selected to improve CoQ10 compound stability and to adjust consistency when required. In one embodiment, the preferred pH value is about 3.0 to about 7.4, more preferably about 3.0 to about 6.5, most preferably from about 3.5 to about 6.0.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Other known transdermal skin penetration enhancers can also be used to facilitate delivery of CoQ10. Illustrative are sulfoxides such as dimethylsulfoxide (DMSO) and the like; cyclic amides such as 1-dodecylazacycloheptane-2-one (Azone™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltrimethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, a-pinene, β-carene, α-terpineol, carvol, carvone, menthone, limonene oxide, a-pinene oxide, eucalyptus oil, and the like.

Also suitable as skin penetration enhancers are organic acids and esters such as salicyclic acid, methyl salicylate, citric acid, succinic acid, and the like.

Angiogenesis and Angiogenesis-Dependent Diseases

As used herein, the terms "angiogenesis inhibitory", "angiogenesis inhibiting" or "anti-angiogenic" include vasculogenesis, and are intended to mean effecting a decrease in the extent, amount, or rate of neovascularization. Effecting a decrease in the extent, amount, or rate of endothelial cell proliferation or migration in the tissue is a specific example of inhibiting angiogenesis.

The term "angiogenesis inhibitory composition" refers to a composition comprising CoQ10 which inhibits tumor mediated angiogenesis processes such as endothelial cell migration, proliferation, tube formation and subsequently leading to the inhibition of the generation of new blood vessels from existing ones, and consequently the inhibition of angiogenesis-dependent diseases, for example, angiogenesis mediated by tumors. See, for example FIGS. 29A and 29B wherein a composition comprising CoQ10 inhibits tumor-mediated angiogenesis in a tissue as compared to control tissue in the absence of any CoQ10. The composition comprising CoQ10 is described in detail in the examples which follow.

As used herein, the term "angiogenesis-dependent disease" is intended to mean a disease where the process of angiogenesis or vasculogenesis sustains or augments a pathological condition. In particular, angiogenesis-dependent disease refers to tumor-mediated angiogenesis.

Angiogenesis is the formation of new blood vessels from pre-existing capillaries or post-capillary venules. Vasculogenesis results from the formation of new blood vessels arising from angioblasts which are endothelial cell precursors. Both processes result in new blood vessel formation and are included in the meaning of the term angiogenesis-dependent diseases. Similarly, the term "angiogenesis" as used herein is intended to include de novo formation of vessels such as that arising from vasculogenesis as well as those arising from branching and sprouting of existing vessels, capillaries and venules.

Angiogenesis, including vasculogenesis, is an important physiological process, without which embryonic development and wound healing would not occur. However, angiogenesis is also inappropriately recruited into numerous pathological conditions as a means to provide adequate blood and nutrient supply to the cells within the affected tissue. Many of these pathological conditions involve aberrant cell proliferation or regulation. Such conditions in which angiogenesis is believed to be important are referred to herein as angiogenesis-dependent diseases. However, methods of the invention also can be used beneficially to inhibit angiogenesis associated with normal physiological processes. For example, the inhibition of angiogenesis associated with the menstrual cycle can be prophylactically used as an effective method of birth control. Therefore, the description below in reference to the treatment of angiogenesis-dependent diseases are also applicable to the inhibition of normal angiogenic responses where a prophylactic or therapeutic need or benefit exists.

Angiogenesis-dependent diseases include, for example, inflammatory disorders such as immune and non-immune inflammation, rheumatoid arthritis, chronic articular rheumatism and psoriasis; disorders associated with inappropriate or inopportune invasion of vessels such as diabetic retinopathy, neovascular glaucoma, retinopathy of prematurity, macular degeneration, corneal graft rejection, retrolental fibroplasia, rubeosis, capillary proliferation in atherosclerotic plaques and osteoporosis; and cancer associated disorders, including for example, solid tumors, tumor metastases, blood born tumors such as leukemias, angiofibromas, Kaposi sarcoma, benign tumors such as hemangiomas, acoustic neuromas, neurofibromas, trachomas, and pyogenic granulomas, as well as other cancers which require neovascularization to support tumor growth. Additional examples of angiogenesis-dependent diseases include, for example, Osler-Webber Syndrome; myocardial angiogenesis; plaque neovascularization; telangiectasia; hemophiliac joints and wound granulation. Other diseases in which angiogenesis plays a role in the maintenance or progression of the pathological state are known to those skilled in the art and are similarly intended to be included within the meaning of the term used herein. Preferably, angiogenesis-mediated diseases refers to tumor induced angiogenesis.

In Vitro Biological Assay of Angiogenesis Inhibiting Activity

The CoQ10 compounds of the instant invention can be tested for their angiogenesis inhibiting activity in several assay systems in vitro and are well within the knowledge of one of ordinary skill in the art. Endothelial cells, for example, human umbilical vein endothelial cells (HUVEC) or human microvascular endothelial cells (HMVEC) can be prepared or obtained commercially, are mixed at a concentration of $2 \times 10^5$ cells/mL with fibrinogen (5 mg/mL in phosphate buffered saline (PBS) in a 1:1 (v/v) ratio. Thrombin is added (5 units/mL final concentration) and the mixture immediately transferred to a 24-well plate (0.5 mL per well). The fibrin gel is allowed to form and then vascular endothelial growth factor (VEGF) and fibroblast growth factor basic (FGF2) are added to the wells (each at 5 ng/mL final concentration) along with the test compound, as described in the Examples which follow. The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g., 0 or 1 branch). This assay is recognized in the art to be predictive of angiogenic efficacy (or angiogenesis inhibiting activity) in vivo (Grant et al., *In Vitro Cell Dev. Biol.* 27A:327-336 (1991); MM et al., *Cancer Res.* 56:2428-2433 (1996)).

In an alternate assay, endothelial cell tube formation is observed when endothelial cells are cultured on Matrigel™ matrix-coated plates, commercially available from Becton Dickinson of Bedford, Pa. (Schnaper et al., *J. Cell. Physiol.* 165:107-118 (1995)). Endothelial cells ($1 \times 10^4$ cells/well) are transferred onto Matrigel™ matrix-coated 24-well plates, and tube formation is quantitated after 48 hours Inhibitors are tested by adding them either at the same time as the endothelial cells or at various time points thereafter.

This assay models angiogenesis by presenting to the endothelial cells a particular type of basement membrane, namely the layer of matrix which migrating and differentiating endothelial cells might be expected to first encounter. In addition to bound growth factors, the matrix components found in Matrigel™ matrix (and in basement membranes in situ) or proteolytic products thereof may also be stimulatory for endothelial cell tube formation which makes this model complementary to the fibrin gel angiogenesis model.

Additionally, angiogenic activities of compounds of the present invention can be evaluated by the chick chorioallantoic membrane (CAM) assay (Oikawa et al, *Cancer Lett.* 59:57-66 (1991)).

Combination Therapies

The CoQ10 therapeutic compositions of the present invention may be combined with any other methods generally employed in the treatment of the particular tumor, disease or disorder that the patient exhibits. So long as a particular therapeutic approach is not known to be detrimental to the patient's condition in itself, and does not significantly counteract the CoQ10 composition treatment, its combination with the present invention is contemplated.

In connection solid tumor treatment, the present invention may be used in combination with classical approaches, such as surgery, radiotherapy, chemotherapy, and the like. The invention therefore provides combined therapies in which the CoQ10 therapeutic compositions are used simultaneously with, before, or after surgery or radiation treatment; or are administered to patients with, before, or after conventional chemotherapeutic, radiotherapeutic or other anti-angiogenic agents, or targeted immunotoxins or coaguligands.

Combination therapy for other vascular diseases is also contemplated. A particular example of such is benign prostatic hyperplasia (BPH), which may be treated with CoQ10 compositions in combination other treatments currently practiced in the art. For example, targeting of immunotoxins to markers localized within BPH, such as PSA.

When one or more agents are used in combination with the CoQ10 compositions, there is no requirement for the combined results to be additive of the effects observed when each treatment is conducted separately. Although at least additive effects are generally desirable, any increased anti-tumor effect above one of the single therapies would be of benefit. Also, there is no particular requirement for the combined treatment to exhibit synergistic effects, although this is certainly possible and advantageous.

To practice combined anti-tumor therapy, one would simply administer to an animal a the CoQ10 composition construct in combination with another anti-cancer agent in a manner effective to result in their combined anti-tumor actions within the animal. The agents would therefore be provided in amounts effective and for periods of time effective to result in their combined presence within the tumor vasculature and their combined actions in the tumor environment. To achieve this goal, the CoQ10 compositions and other anti-cancer agents may be administered to the animal simultaneously, either in a single composition, or as two distinct compositions using different administration routes.

Alternatively, the CoQ10 composition mediated treatment may precede, or follow, the a second anti-cancer agent treatment by, e.g., intervals ranging from minutes to weeks. In certain embodiments where the anti-cancer agent and the CoQ10 composition are applied separately to the animal, one would ensure that a significant period of time did not expire between the time of each delivery, such that the anti-cancer agent and the CoQ10 composition would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

The general use of combinations of substances in cancer treatment is well known. For example, U.S. Pat. No. 5,710,134 (incorporated herein by reference) discloses components that induce necrosis in tumors in combination with non-toxic substances or "prodrugs". The enzymes set free by necrotic processes cleave the non-toxic "prodrug" into the toxic "drug", which leads to tumor cell death. Also, U.S. Pat. No. 5,747,469 (incorporated herein by reference) discloses the combined use of viral vectors encoding p53 and DNA damaging agents. Any such similar approaches can be used with the present invention.

In some situations, it may even be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the CoQ10 composition treatment, and another treatment was intended to prevent micrometastasis or tumor re-growth, such as the administration of an anti-angiogenic agent.

It also is envisioned that more than one administration of either the CoQ10 composition or another anti-cancer agent will be utilized. The CoQ10 composition and anti-cancer agents may be administered interchangeably, on alternate days or weeks; or a sequence of the CoQ10 composition treatment may be given, followed by a sequence of anti-cancer agent therapy. In any event, to achieve tumor regression using a combined therapy, all that is required is to deliver both agents in a combined amount effective to exert an anti-tumor effect, irrespective of the times for administration.

In terms of surgery, any surgical intervention may be practiced in combination with the present invention. In connection with radiotherapy, any mechanism for inducing DNA damage locally within tumor cells is contemplated, such as y-irradiation, X-rays, UV-irradiation, microwaves and even electronic emissions and the like. The directed delivery of radioisotopes to tumor cells is also contemplated, and this may be used in connection with a targeting antibody or other targeting means.

Cytokine therapy also has proven to be an effective partner for combined therapeutic regimens. Various cytokines may be employed in such combined approaches. Examples of cytokines include IL-1a, IL-1$\beta$, IL-2, IL-3, IL-4, IL-5, IL-6, IL-7, IL-8, IL-9, IL-10, IL-11, IL-12, IL-13, TGF-$\beta$, GM-CSF, M-CSF, G-CSF, TNF$\alpha$, TNF$\beta$, LAF, TCGF, BCGF, TRF, BAF, BDG, MP, LIF, OSM, TMF, PDGF, IFN-$\alpha$, IFN-$\beta$, IFN-$\gamma$. Cytokines are administered according to standard regimens, consistent with clinical indications such as the condition of the patient and relative toxicity of the cytokine. Uteroglobins may also be used to prevent or inhibit metastases (U.S. Pat. No. 5,696,092; incorporated herein by reference).

CoQ10 Compositions and Combination Chemotherapeutics

In certain embodiments, the CoQ10 composition of the present invention may be administered in combination with another chemotherapeutic agent. Irrespective of the underlying mechanism(s), a variety of chemotherapeutic agents may be used in the combined treatment methods disclosed herein. Therapeutic agents can include, for example, chemotherapeutic agents such as, cyclophosphamide (CTX, 25 mg/kg/day,p.o.), taxanes (paclitaxel or docetaxel), busulfan, cisplatin, methotrexate, daunorubicin, doxorubicin, melphalan, cladribine, vincristine, vinblastine, chlorambucil, tamoxifen, taxol, etoposide (VP-16), adriamycin, 5-fluorouracil (5FU), camptothecin, actinomycin-D, mitomycin C, cisplatin (CDDP), combretastatin(s) and derivatives and prodrugs thereof.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

The skilled artisan is directed to "Remington's Pharmaceutical Sciences" 15th Edition, chapter 33, in particular pages 624-652, for non-limiting examples of other chemotherapeutic agents that can be used in combination therapies with the CoQ10 compositions. Some variation in dosage will necessarily occur depending on the condition of the subject being treated. The physician responsible for administration will be able to determine the appropriate dose for the individual subject.

Anti-Angiogenics

The term "angiogenesis" refers to the generation of new blood vessels, generally into a tissue or organ. Under normal physiological conditions, humans or animals undergo angiogenesis only in very specific restricted situations. For example, angiogenesis is normally observed in wound healing, fetal and embryonic development and formation of the corpus luteum, endometrium and placenta. Uncontrolled (persistent and/or unregulated) angiogenesis is related to various disease states, and occurs during tumor growth and metastasis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

As persistent, unregulated angiogenesis occurs during tumor development and metastasis, the treatment methods of this invention may be used in combination with any one or more "anti-angiogenic" therapies. Exemplary anti-angiogenic agents that are useful in connection with combined therapy are listed in Table 1. Each of the agents listed therein is exemplary and by no means limiting.

TABLE 1

Inhibitors and Negative Regulators of Angiogenesis Substances

Angiostatin
Endostatin
16 kDa prolactin fragment
Laminin peptides
Fibronectin peptides
Tissue metalloproteinase inhibitors (TIMP 1, 2, 3, 4)
Plasminogen activator inhibitors (PAI-1, -2)
Tumor necrosis factor alpha
(high dose, in vitro)
TGF-β1
Interferons (IFN-α, -β, γ)
ELR-CXC Chemokines: IL-12; SDF-1; MIG,
Platelet factor 4 (PF-4);
IP-10
Thrombospondin (TSP)
SPARC
2-Methoxyoestradiol
Proliferin-related protein
Suramin
Thalidomide
Cortisone
Fumagillin (AGM-1470; TNP-470)

TABLE 1-continued

Inhibitors and Negative Regulators of Angiogenesis Substances

Tamoxifen
Korean mistletoe extract (*Viscum album coloratum*)
Retinoids
CM101
Dexamethasone
Leukemia inhibitory factor (LIF)

A certain preferred component for use in inhibiting angiogenesis is a protein named "angiostatin". This component is disclosed in U.S. Pat. Nos. 5,776,704; 5,639,725 and 5,733,876, each incorporated herein by reference. Angiostatin is a protein having a molecular weight of between about 38 kD and about 45 kD, as determined by reducing polyacrylamide gel electrophoresis, which contains approximately Kringle regions 1 through 4 of a plasminogen molecule. Angiostatin generally has an amino acid sequence substantially similar to that of a fragment of murine plasminogen beginning at amino acid number 98 of an intact murine plasminogen molecule.

The amino acid sequence of angiostatin varies slightly between species. For example, in human angiostatin, the amino acid sequence is substantially similar to the sequence of the above described murine plasminogen fragment, although an active human angiostatin sequence may start at either amino acid number 97 or 99 of an intact human plasminogen amino acid sequence. Further, human plasminogen may be used, as it has similar anti-angiogenic activity, as shown in a mouse tumor model.

Certain anti-angiogenic therapies have already been shown to cause tumor regressions, and angiostatin is one such agent. Endostatin, a 20 kDa COOH-terminal fragment of collagen XVIII, the bacterial polysaccharide CM101, and the antibody LM609 also have angiostatic activity. However, in light of their other properties, they are referred to as anti-vascular therapies or tumor vessel toxins, as they not only inhibit angiogenesis but also initiate the destruction of tumor vessels through mostly undefined mechanisms. Their combination with the present invention is clearly envisioned.

Angiostatin and endostatin have become the focus of intense study, as they are the first angiogenesis inhibitors that have demonstrated the ability to not only inhibit tumor growth but also cause tumor regressions in mice. There are multiple proteases that have been shown to produce angiostatin from plasminogen including elastase, macrophage metalloelastase (MME), matrilysin (MMP-7), and 92 kDa gelatinase B/type TV collagenase (MMP-9).

MME can produce angiostatin from plasminogen in tumors and granulocyte-macrophage colony-stimulating factor (GMCSF) upregulates the expression of MME by macrophages inducing the production of angiostatin. The role of MME in angiostatin generation is supported by the finding that MME is in fact expressed in clinical samples of hepatocellular carcinomas from patients. Another protease thought to be capable of producing angiostatin is stromelysin-1 (MMP-3). MMP-3 has been shown to produce angiostatin-like fragments from plasminogen in vitro.

CM101 is a bacterial polysaccharide that has been well characterized in its ability to induce neovascular inflammation in tumors. CM101 binds to and cross-links receptors expressed on dedifferentiated endothelium that stimulates the activation of the complement system. It also initiates a cytokine-driven inflammatory response that selectively targets the tumor. It is an antipathoangiogenic agent that downregulates the expression VEGF and its receptors.

Thrombospondin (TSP-1) and platelet factor 4 (PF4) may also be used in combination with the present invention. These are both angiogenesis inhibitors that associate with heparin and are found in platelet a-granules. TSP-1 is a large 450 kDa multi-domain glycoprotein that is constituent of the extracellular matrix. TSP-1 binds to many of the proteoglycan molecules found in the extracellular matrix including, HSPGs, fibronectin, laminin, and different types of collagen. TSP-1 inhibits endothelial cell migration and proliferation in vitro and angiogenesis in vivo. TSP-1 can also suppress the malignant phenotype and tumorigenesis of transformed endothelial cells. The tumor suppressor gene p53 has been shown to directly regulate the expression of TSP-1 such that, loss of p53 activity causes a dramatic reduction in TSP-1 production and a concomitant increase in tumor initiated angiogenesis.

PF4 is a 70aa protein that is member of the CXC ELR-family of chemokines that is able to potently inhibit endothelial cell proliferation in vitro and angiogenesis in vivo. PF4 administered intratumorally or delivered by an adenoviral vector is able to cause an inhibition of tumor growth.

Interferons and metalloproteinase inhibitors are two other classes of naturally occurring angiogenic inhibitors that can be combined with the present invention. The anti-endothelial activity of the interferons has been known since the early 1980s, however, the mechanism of inhibition is still unclear. It is known that they can inhibit endothelial cell migration and that they do have some anti-angiogenic activity in vivo that is possibly mediated by an ability to inhibit the production of angiogenic promoters by tumor cells. Vascular tumors in particular are sensitive to interferon, for example, proliferating hemangiomas can be treated with IFNα.

Tissue inhibitors of metalloproteinases (TIMPs) are a family of naturally occurring inhibitors of matrix metalloproteases (MMPs) that can also inhibit angiogenesis and can be used in combined treatment protocols with the present invention. MMPs play a key role in the angiogenic process as they degrade the matrix through which endothelial cells and fibroblasts migrate when extending or remodeling the vascular network. In fact, one member of the MMPs, MMP-2, has been shown to associate with activated endothelium through the integrin avβ3 presumably for this purpose. If this interaction is disrupted by a fragment of MMP-2, then angiogenesis is downregulated and in tumors growth is inhibited.

There are a number of pharmacological agents that inhibit angiogenesis, any one or more of which may be used in combination with the present invention. These include AGM-1470/TNP-470, thalidomide, and carboxyamidotriazole (CAI). Fumagillin was found to be a potent inhibitor of angiogenesis in 1990, and since then the synthetic analogues of funagillin, AGM-1470 and TNP-470 have been developed. Both of these drugs inhibit endothelial cell proliferation in vitro and angiogenesis in-vivo. TNP-470 has been studied extensively in human clinical trials with data suggesting that long-term administration is optimal.

Thalidomide was originally used as a sedative but was found to be a potent teratogen and was discontinued. In 1994 it was found that thalidomide is an angiogenesis inhibitor. Thalidomide is currently in clinical trials as an anti-cancer agent as well as a treatment of vascular eye diseases.

CAI is a small molecular weight synthetic inhibitor of angiogenesis that acts as a calcium channel blocker that prevents actin reorganization, endothelial cell migration and spreading on collagen IV. CAI inhibits neovascularization at physiologically attainable concentrations and is well tolerated orally by cancer patients. Clinical trials with CAI have yielded disease stabilization in 49% of cancer patients having progressive disease before treatment.

Cortisone in the presence of heparin or heparin fragments was shown to inhibit tumor growth in mice by blocking endothelial cell proliferation. The mechanism involved in the additive inhibitory effect of the steroid and heparin is unclear although it is thought that the heparin may increase the uptake of the steroid by endothelial cells. The mixture has been shown to increase the dissolution of the basement membrane underneath newly formed capillaries and this is also a possible explanation for the additive angiostatic effect. Heparin-cortisol conjugates also have potent angiostatic and anti-tumor effects activity in vivo.

Further specific angiogenesis inhibitors, including, but not limited to, Anti-Invasive Factor, retinoic acids and paclitaxel (U.S. Pat. No. 5,716,981; incorporated herein by reference); AGM-1470 (Ingber et al., Nature, 48:555-557 1990; incorporated herein by reference); shark cartilage extract (U.S. Pat. No. 5,618,925; incorporated herein by reference); anionic polyamide or polyurea oligomers (U.S. Pat. No. 5,593,664; incorporated herein by reference); oxindole derivatives (U.S. Pat. No. 5,576,330; incorporated herein by reference); estradiol derivatives (U.S. Pat. No. 5,504,074; incorporated herein by reference); and thiazolopyrimidine derivatives (U.S. Pat. No. 5,599,813; incorporated herein by reference) are also contemplated for use as anti-angiogenic compositions for the combined uses of the present invention.

Compositions comprising an antagonist of an $a_vB_3$ integrin may also be used to inhibit angiogenesis in combination with the present invention. As disclosed in U.S. Pat. No. 5,766,591 (incorporated herein by reference), RGD-containing polypeptides and salts thereof, including cyclic polypeptides, are suitable examples of $a_vB_3$ integrin antagonists.

The antibody LM609 against the $a_vB_3$ integrin also induces tumor regressions. Integrin $a_vB_3$ antagonists, such as LM609, induce apoptosis of angiogenic endothelial cells leaving the quiescent blood vessels unaffected. LM609 or other $a_vB_3$ antagonists may also work by inhibiting the interaction of $a_vB_3$ and MMP-2, a proteolytic enzyme thought to play an important role in migration of endothelial cells and fibroblasts.

Apoptosis of the angiogenic endothelium in this case may have a cascade effect on the rest of the vascular network Inhibiting the tumor vascular network from completely responding to the tumor's signal to expand may, in fact, initiate the partial or full collapse of the network resulting in tumor cell death and loss of tumor volume. It is possible that endostatin and angiostatin function in a similar fashion. The fact that LM609 does not affect quiescent vessels but is able to cause tumor regressions suggests strongly that not all blood vessels in a tumor need to be targeted for treatment in order to obtain an anti-tumor effect.

Non-targeted angiopoietins, such as angiopoietin-2, may also be used in combination with the present invention. The angiogenic effects of various regulators involve an autocrine loop connected with angiopoietin-2. The use of angiopoietin-2, angiopoietin-1, angiopoietin-3 and angiopoietin-4, is thus contemplated in conjunction with the present invention. Other methods of therapeutic intervention based upon altering signaling through the Tie2 receptor can also be used in combination herewith, such as using a soluble Tie2 receptor capable of blocking Tie2 activation (Lin et al., Proc. Natl. Acad. Sci., USA, 95(15):8829-34, 1998). Delivery of such a construct using recombinant adenoviral gene therapy has been shown to be effective in treating cancer and reducing metastases (Lin et al., 1998).

CoQ10 Compositions and Combination Therapy with Apoptosis-Inducing Agents

The CoQ10 composition treatment may also be combined with treatment methods that induce apoptosis in any cells within the tumor, including tumor cells and tumor vascular endothelial cells. Although many anti-cancer agents may have, as part of their mechanism of action, an apoptosis-inducing effect, certain agents have been discovered, designed or selected with this as a primary mechanism, as described below.

A number of oncogenes have been described that inhibit apoptosis, or programmed cell death. Exemplary oncogenes in this category include, but are not limited to, bcr-abl, bcl-2 (distinct from bcl-1, cyclin D1; GenBank accession numbers M14745, X06487; U.S. Pat. Nos. 5,650,491; and 5,539,094; each incorporated herein by reference) and family members including Bcl-xl, Mcl-1, Bale, Al, A20. Overexpression of bcl-2 was first discovered in T cell lymphomas. bcl-2 functions as an oncogene by binding and inactivating Bax, a protein in the apoptotic pathway Inhibition of bcl-2 function prevents inactivation of Bax, and allows the apoptotic pathway to proceed. Thus, inhibition of this class of oncogenes, e.g., using antisense nucleotide sequences, is contemplated for use in the present invention in aspects wherein enhancement of apoptosis is desired (U.S. Pat. Nos. 5,650,491; 5,539,094; and 5,583,034; each incorporated herein by reference).

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, provision of tumor suppressors is also contemplated for use in the present invention to stimulate cell death. Exemplary tumor suppressors include, but are not limited to, p53, Retinoblastoma gene (Rb), Wilm's tumor (WT1), bax alpha, interleukin-1β-converting enzyme and family, MEN-1 gene, neurofibromatosis, type 1 (NF1), cdk inhibitor p16, colorectal cancer gene (DCC), familial adenomatosis polyposis gene (FAP), multiple tumor suppressor gene (MTS-l), BRCA1 and BRCA2.

Preferred for use are the p53 (U.S. Pat. Nos. 5,747,469; 5,677,178; and 5,756,455; each incorporated herein by reference), Retinoblastoma, BRCA1 (U.S. Pat. Nos. 5,750,400; 5,654,155; 5,710,001; 5,756,294; 5,709,999; 5,693,473; 5,753,441; 5,622,829; and 5,747,282; each incorporated herein by reference), MEN-1 (GenBank accession number U93236) and adenovirus EIA (U.S. Pat. No. 5,776,743; incorporated herein by reference) genes.

Other compositions that may be used include genes encoding the tumor necrosis factor related apoptosis inducing ligand termed. TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1β-converting enzyme and family members, which are also reported to stimulate apoptosis.

Compounds such as carbostyril derivatives (U.S. Pat. Nos. 5,672,603; and 5,464,833; each incorporated herein by reference); branched apogenic peptides (U.S. Pat. No. 5,591,717; incorporated herein by reference); phosphotyrosine inhibitors and non-hydrolyzable phosphotyrosine analogs (U.S. Pat. Nos. 5,565,491; and 5,693,627; each incorporated herein by reference); agonists of RXR retinoid receptors (U.S. Pat. No. 5,399,586; incorporated herein by reference); and even antioxidants (U.S. Pat. No. 5,571,523; incorporated herein by reference) may also be used. Tyrosine kinase inhibitors, such as genistein, may also be linked to ligands that target a cell surface receptor (U.S. Pat. No. 5,587,459; incorporated herein by reference).

Effective Amounts

The compositions described above are preferably administered to a subject in an effective amount. An effective amount is an amount which is capable of producing a desirable result in a treated animal or cell (for example, to induce apoptosis or impair mitosis in a cell in the animal or a culture). As is well known in the medical and veterinary arts, dosage for any one animal depends on many factors, including the particular animal's size, body surface area, age, the particular composition to be administered, time and route of administration, general health, and other drugs being administered concurrently. It is expected that an appropriate dosage for topical administration of the compositions of the invention would be in the range of about 1.5-4.0 mg CoQ10/kg of body weight (e.g., 200 mg for subjects ranging from 110 to 300 lbs.). An effective amount for use with a cell in culture will also vary, but can be readily determined empirically (for example, by adding varying concentrations to the cell and selecting the concentration that best produces the desired result). It is expected that an appropriate concentration would be in the range of about 5-200 µM.

Method for Inhibiting Cancer Cell Growth

The invention provides a method for inhibiting tumor cell growth or increasing the rate of tumor cell apoptosis. The method includes the steps of contacting a tumor cell with a composition including a sufficient amount of CoQ10 to kill or at least retard mitosis in the tumor cell. The method may be used to inhibit the growth of numerous types of cancerous tumor cells. Coenzyme Q10 has been tested and shown to be effective against melanoma, squamous, and breast cancer cells. Coenzyme Q10 is expected to be effective against other cancers as well, particularly those derived from epithelial, mesenchymal, and hemopoietic origins.

Any suitable formulation of CoQ10 can be used in methods of the invention. Typical formulations are topical liposomal formulations of coenzyme Q10 of varying concentrations. In addition to topical administration, CoQ10-containing formulations can be administered to a subject via injection (e.g., IP, IV, IM, SQ).

In a method of reducing the rate of tumor cell growth or increasing the rate of tumor cell apoptosis in vitro, CoQ10 is dissolved in 2-propanol followed by dilution in a desired medium (as described in example 1 below). In an in vivo method of reducing the rate of tumor cell growth or increasing the rate of tumor cell apoptosis, a CoQ10-containing cream is applied topically daily to the target site until tumor regression occurs (as described in examples 2 and 3). In another in vivo method, a CoQ10-containing formulation is administered to a subject via injection (e.g., EP, IV, IM, SQ).

Inhibition of tumor cell growth manifested by administration of the CoQ10 compositions described herein, that is compositions comprising about 1% to about 25% coenzyme Q10, refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

In preferred embodiments, administration of coenzyme Q10 compositions results in one or more phenotypes of a tumor cell being inhibited. For example, inhibition of tumor growth, reduction of tumor size, inhibition of metastasis, reduction in the number of tumor cells and the like. Each of these phenotypes of a tumor cell can be measured using standard assays, such as for example, imaging, mechanical measurements, in vitro assays and the like.

Kits and Formulations

The invention also provides a kit for reducing the rate of tumor growth in a subject. The kit of the invention includes a composition comprising CoQ10 and a pharmaceutically acceptable carrier as well as printed instructions for using the composition to reduce the rate of tumor growth in a subject.

Active components can be present in solid, semi-solid or liquid form. Solid forms include for example, powders, granules and flakes. Semi-solid forms include, for example, gels, creams, gelatins and ointments. These and other active agents embraced by the present invention are known to those of ordinary skill in the art and, in most cases, are commercially available from suppliers such as Compound Solutions, Inc., Escondido, Calif. Information on these and other active and inactive agents embraced by the invention, and their commercial suppliers is available from various trade manuals, most particularly, Remington's Pharmaceutical Sciences, United States Pharmacopoeia (USP), National Formulary (NF), Merck Index, Physician's Desk Reference (PDR) and Chemical Abstracts.

The kits of the invention will also generally contain at least one inactive agent. As used herein, inactive agents are agents which do not provide any therapeutic benefit to the subject to whom they are administered. Instead, inactive agents can function in many other ways such as to provide a base in which the active agent can be dissolved or suspended, to dilute the active agent in order to provide proper doses upon administration, to facilitate the dissolution or suspension of the active agent, or to prevent oxidation of the active agent by removing air bubbles from the final compounded suspension. In some embodiments of the invention, the kits lack an inactive agent, and rather contain two or more active agents.

Base agents such as creams, oils, gels or ointments are suitable for topical or suppository applications. The choice of suitable inactive base agent for use in the kits of the invention will depend upon the active agent to be compounded. Suitable base agents will be known to the ordinary artisan. Alternatively, Remington's Pharmaceutical Sciences, the Physician Desk Reference (PDR) or other manuals as listed above, can be consulted in making this determination.

Examples of inactive base agents or components include, for example, lanolin, hydrophilic ointment, white ointment, yellow ointment, polyethylene glycol ointment, petrolatum, hydrophilic petrolatum, white petrolatum, rose water ointment, squalene, hydrogenated vegetable oil (Type II), ultrasound gel, pluronic lecithin organogel (PLO) gel, cream.

The term "petrolatum" as used herein means petrolatum ointment, petrolatum gel or petrolatum cream, all of which are commercially available. It is well within the realm of the ordinary pharmaceutical artisan to determine which form of petrolatum is most appropriate for a specific kit.

A commercially available ultrasound base is either POLYSONIC™ (ultrasound gel) ultrasound lotion or Aquasonic ultrasound 100 gel manufactured by Parker Laboratories, Inc. (Fairfield, N.J.) or EcoGel 100 or EcoGel 200 manufactured by Eco-Med (Mississauga, Ontario, Canada), the compositions of which may include cetyl alcohol, liquid paraffin, polymer, surfactants, preservatives such as propyl paraben and methyl paraben in bacteriostatic concentration, fragrance, and reverse osmosis water. As used herein, a gel is a base with a higher viscosity than a lotion. The physical characteristics of the POLYSONIC™ (ultrasound gel) ultrasound lotion and the EcoGel 100 include pH range of 6.5-7.0, density of 1.04 g/cm$^3$, viscosity of 35,000 to 70,000 cps and acoustic impedence of 1.60 (10$^5$ g/cm$^2$ sec). The physical characteristics of Aquasonic ultrasound 100 gel or EcoGel 200 are similar to those of POLYSONIC™ (ultrasound gel) ultrasound lotion and EcoGel 100 except that their viscosity is 80,000 to 110,000 cps. These lotions and gels are available in a clear, colorless form or in a blue colored form.

Liquid bases are recommended for orally administered pharmaceuticals. In some embodiments of the invention, at least one active agent, e.g. CoQ10, will be supplied already co-mingled with an inactive agent. Examples of this include the combination of magnesium hydroxide and aluminum hydroxide (commercially available as MAALOX™ (magnesium hydroxide/aluminum hydroxide)), and diphenhydramine HCl (commercially available as BENADRYL™ (diphenhydramine hydrochloride)). Both MAALOX™ (magnesium hydroxide/aluminum hydroxide) and BENADRYL™ (diphenhydramine hydrochloride) are supplied by their respective manufacturers as a combination of active and inactive agents.

Sterile base solutions are preferred for parenteral (i.e., injection), aerosol (i.e., inhalation) and ophthalmic routes of administration. The administration may, for example, be intravenous, intraperitoneal, intramuscular, intracavity, subcutaneous or transdermal. Preparations for parenteral administration includes sterile aqueous or nonaqueous solutions, suspensions and emulsions. The compounded pharmaceuticals, preferably those intended for parenteral, inhalation or ophthalmic routes of administration, may be prepared and administered in inactive agents which are pharmaceutically-acceptable. As used herein, a pharmaceutically-acceptable carrier means a non-toxic material that does not interfere with the effectiveness of the biological activity of the active agents and that is compatible with the biological systems such of a tissue or organism. The physiologically acceptable carrier must be sterile for in vivo administration. Pharmaceutically acceptable carriers include diluents, fillers, salts, buffers, stabilizers, solubilizers and other materials which are well-known in the art. The characteristics of the carrier will depend on the route of administration. In general, pharmaceutically-acceptable agents or carriers are well-known to those of ordinary skill in the art. In some embodiments, suitable sterile solutions include albuterol and ipratropium inhalation solution; papaverine, phentolamine and prostaglandin injection solution; fentanyl citrate injection solution and cyclosporine ophthalmic drops.

Examples of nonaqueous solvents are propylene glycol, polyethylene glycol, vegetable oil such as olive oil, an injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents, and inert gases and the like. Those of skill in the art can readily determine the various parameters for preparing these alternative pharmaceutical compositions without resort to undue experimentation.

Inactive agents may also include components which function to preserve the integrity of the compounded formulation. This latter category of inactive agents includes, for example, anti-foaming agents. Anti-foaming agents are agents which function to remove unwanted air trapped in a composition, perhaps during mixing or agitation. The use of anti-foaming components is particularly useful in the preparation of pharmaceuticals to be used for ultrasound imaging due to the impedance of signal transmission by air bubbles. Examples of other anti-foaming agents useful in the compositions of the invention include bisphenylhexamethicone, dimethicone, dimethiconol, hexamethyldisiloxane, hexyl alcohol, isopropyl alcohol, petroleum distillates, phenethyl disiloxane, phenyl trimethicone, polysilicone-7, propyl alcohol, silica dimethyl silylate, silica silylate, tetramethyl decynediol and trimethylsiloxysilicate. A preferred anti-foaming agent is simethicone. Simethicone is a mixture of about 90% dimethicone and 10% silicone dioxide (w/w). Simethicone is used extensively as an anti-gas agent in pharmaceutical products such as GAS-X™ (simethicone), MAALOX™ (magnesium hydroxide/aluminum hydroxide), MYLANTA™ (aluminum, magnesium simethicone), PHAZYME™ (simethicone), GENAZYME™ (simethicone), and MYLICON™ (simethicone) Drops. Simethicone may be used as an anti-foaming agent in any of the formulations embraced by the invention.

Other inactive agents which can be included in the formulations of the invention include stabilizers such as citric acid, anti-oxidants such as sodium metabisulfite and preservatives such as methyl or propyl paraben.

Another class of inactive agents is suspending agents. Suspending agents are agents which facilitate the suspension and in some cases the dissolution of an active agent in a base. Generally, suspending agents ensure more uniform mixing of active and base components. In order to administer a more uniform dose of a compounded pharmaceutical to a patient, the compounded components must be properly and homogeneously combined. If the active agent is present as a powder, a uniform dispersion is sometimes difficult to achieve using the traditional form of compounding.

A subcategory of suspending agents are solubilizers. Solubilizers are agents which facilitate the dissolution of a solid or, in some cases, a semi-solid agent in a base inactive agent. In some embodiments of the invention, a solid-form active agent may be dissolved in a suspending agent, prior to mixing it with the base agent. Conversely, the suspending agent and the base agent may be prepackaged together, particularly if the concern is ensuring the uniform blending of active agent within the base component rather than the loss of solid (i.e., powdery) active agent. In still other variations, the suspending agent may be premixed with the base inactive agent.

Suitable suspending agents useful in the compositions of the invention include, but are not limited to, glycerin, hexylene glycol, propylene glycol, sorbitol, acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monstearate, stearic acid, trolamine, emulsifying wax, benzalkonium chloride, benzethonium chloride, cetylpyridinium chloride, docusate sodium, nonoxynol 9, nonoxynol 10, octoxynol 9, polyoxyl 50 stearate, and tyloxapol.

Still other suspending agents include humectants and wetting agents. Humectants are agents which retain moisture. Examples of humectants include but are not limited to glycerin, hexylene glycol, propylene glycol and sorbitol. The amounts of base and non-base inactive agents will also depend upon the particular compounded pharmaceutical to be made. Base agents can be provided in quantities corresponding to final compounded preparations which contain 0.5% to 99.99% of base agent, either in weight or in volume. In preferred embodiments, the final concentration of the base agent is 20%-80%. In even more preferred embodiments, the final concentration of the base agent is 40%-80%.

Generally, the amounts of non-base agents will be sufficient to provide final formulations in which each non-base inactive agent represents 0.01%-50% (w/w) of the composition. Suspending agents may represent 1%-50% (w/w) of the final formulation. Preferably, suspending agents will represent 1%-40% and even more preferably, they will represent 5%-30% of the final formulation. Anti-foaming agents may represent 0.01% to 20% (w/w) of the final formulation. More preferably, anti-foaming agents represent 0.05% to 10% of the final formulation and even more preferably, they represent 0.1% to 5% of the final formulation.

In some preferred embodiments, the single or multiple unit of use kits are designed to yield, after the physical mixing of active and inactive agents, compounded pharmaceutical formulations comprising 1%, 5%, 10% or 20% w/w of CoQ10.

The kits of the invention will provide each and every component required for preparing a given compounded pharmaceutical in pre-measured quantities. The measuring of each component will be performed using current Good Manufacturing Practices (cGMP, as legislated by the Code of Federal Regulations or CFR), as will the packaging and labeling of each component and the final packaging and labeling of the kit in its entirety. In this way, the kits are standardized and variations from batch to batch will be minimal or non-existent and the precision and accuracy in the measurement of individual components will be improved considerably over the methods currently used by pharmacists. Instructions may be provided as separate from any container, but still contained in the kit. Alternatively, instructions may be located on a container, for example, on an exterior surface or on an interior surface such as a lid.

Both the active and the inactive agents of the kit are provided in containers. Since the kit will contain at least one active and at least one inactive agent, or at least two active agents pre-formulated with inactive agents, the minimum number of containers in a given kit will be two. In preferred embodiments, the maximum number of containers in a kit will be less than or equal to four. The containers may be formed in any size or shape useful for the mixing or transferring of components from one container to another. For example, each container may be in the form of vials, bottles, squeeze bottles, jars, sealed sleeves, envelopes or pouches, tubes or blister packages or any other suitable form provided the container is sealed so as to prevent premature mixing of components. As used herein, a container may also be a compartment or a chamber within a vial, a tube, ajar, or an envelope, or a sleeve, or a blister package or a bottle, provided that the contents of one compartment are not able to associate physically with the contents of another compartment prior to their deliberate mixing by a pharmacist or physician.

The invention intends to provide within a single kit all the necessary components, containers and stiffing or mixing elements for preparing a unit of use compounded pharmaceutical without the need for other accessories. The kits of the invention may also contain items such as gloves or spill pads. Individuals skilled in the art can readily modify the choice of container to suit the individual components housed an<i mixed therein.

In some embodiments of the invention, the final compounded formulation will be provided to the patient in the container originally housing the inactive, or base, compound. In other embodiments, the final compounded formulation will be provided in the container originally housing the active agent. In still other embodiments, all the necessary components for preparing a compounded pharmaceutical are included in one container but are physically separated within such a container. For example, an inactive agent may be contained in the lower part of a container, such as ajar, and may be covered by a plastic, peel-off wrap. The active agent maybe housed in this same jar, but secured to the lid of the jar and provided in a pouch or a sleeve. The ability to provide all components together in the smallest packaging arrangement may be preferable in some circumstances. Mixing elements required in the preparation of the compounded pharmaceutical may also be located, within the same container, for example, secured to the inside surface of the lid of the container.

In still another embodiment of the invention, active and inactive agents are provided in adjacent compartments of a single housing container, and are mechanically removed from these compartments and into a third compartment. As an example, all the chemical components necessary to prepare a particular compounded pharmaceutical can be present in a single tube, for example, a tube similar to a toothpaste tube having an interior which is divided into separate compartments. Each of these compartments in turn house a base agent or an active agent. Either the base agent or the active agent may be premixed with an anti-foaming agent and/or a suspending agent, as described herein. By applying pressure on the tube as a whole, the components are made to exit their respective compartments. They can then be mixed either in an adjacent or a physically separate compartment. Squeezing or pressing of the outside surface of the tube maybe all that is necessary to retrieve the individual components housed within the tube. In yet another embodiment, the contents of both chambers of a container can be pumped out and into a third container. In a related embodiment, it is also envisioned that rather than requiring the contents of each compartment to exit and flow into a third compartment, the components may be separated by a removable sheet or film. Thus, upon removal of such a sheet or film, the contents of the two compartments are in contact and may require only agitation or end-over-end inversion to become completely mixed. This latter embodiment would eliminate the need for a mixing element, and potentially for an exterior package particularly if the instructions are written on the container itself.

According to some aspects of the invention, each container may contain one or more active agents or one or more inactive agents. For example, in some embodiments of the invention, none of the containers may contain both an active and an inactive agent prior to mixing by the pharmacist or physician. However, the invention also provides for kits in which a container may contain an active and at least one inactive agent, such as a base agent, a suspending agent or an antifoaming agent.

In a preferred embodiment, the active agent is provided premixed with an inactive agent. This applies mainly when CoQ10 is commercially available as a solid, for example a powder, and the pre-mixing of the powder with a suspending agent facilitates the compounding by the pharmacist or physician. In yet other embodiments, at least two of the inactive agents may be pre-mixed as provided in the kits of the invention.

In some embodiments, where the active agent is added to the base component, it may be desirable to provide the base component in a container which is only partially full. In preferred embodiments, the container in which the base component is situated is less than 100% full by volume. In other embodiments, the containers are 95%, 90%, 80%, 75%, 70%, 60%, 50%, 40%, 30%, 25%, 20% or less than 20% full by volume. In other embodiments, the active or inactive agents comprise a volume of their respective containers ranging from 100% to greater than 1%, and every integer there between. In preferred embodiments, the inactive agent occupies a volume of the second container which is less than or equal to the volume of the second container minus the volume of the active agent.

As used according to the invention, the active and inactive agents are physically combined by a pharmacist to produce a compounded pharmaceutical. The components of the kit can be combined by gentle agitation, shaking, stiffing, folding or end-over-end inversion of the first or second container. In some instances, the proper mixing of the active and inactive agents may be accomplished simply by adding one to the other, followed by sealing and agitation of the container. This is especially the case if the components are both liquids or both semi-solids, hi other instances, it may be necessary to stir the components together with a mixing element. Mixing elements are well known to a person of ordinary skill in the pharmaceutical arts and may include for example, centrifuges, a mixing rod such as a glass rod, a spoon, a spatula or a dipstick. Where required, the mixing element is provided in the kit. The presence of a mixing element will vary depending on the compounded pharmaceutical formulation to be made with the components of a kit.

The final compounded pharmaceutical may be formulated into preparations in solid, semi-solid, liquid or gaseous forms such as tablets, capsules, powders, granules, ointments, solutions, suppositories, inhalants and injections, and usual ways for oral, parenteral or surgical administration. The invention also embraces locally administering the compounded pharmaceuticals of the invention such as, for example, as implants. These formulations may be intended for oral, topical, mucosal, parenteral (e.g., injectable), rectal or vaginal administration. In preferred embodiments, the final compounded formulations may be self-administered.

The kits of the invention may also contain a package which may be compartmentalized to receive in close confinement two or more containers of the invention. In some embodiments, the package may be box-like, being made of a moderately rigid material such as cardboard or reinforced paper. In other embodiments, the package may be a bag. In still other embodiments, as described herein, there is no external packaging and all containers may be incorporated into one of the containers housing either an active or an inactive agent. This latter embodiment can be accomplished by securing containers such as pouches, sleeves or sacs, containing either active or inactive agents, as well as any mixing elements required for the compounding, to the interior of the lid of the main container. An individual skilled in the art can readily modify the package to suit the individual needs of each kit and each use. The kits of the invention further contain instructions for the proper use of the components found therein.

The kits of the invention are intended for use in the treatment or prevention of a number of disorders in a variety of subjects including humans, dogs, cats, horses, fish, pigs, cows, sheep, deer, zoo animals and laboratory animals (e.g., mice, rats, rabbits, monkeys, etc.). The invention intends to embrace unit of use kits containing the above preparations.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

The following examples serve to illustrate the invention without limiting it thereby. It will be understood that variations and modifications can be made without departing from the spirit and scope of the invention.

Example 1

Materials and Methods for Apoptosis Assay

Cell lines used in the assay were SK-Me128 and nFIB. Cells (SK-Me128 and nFB) were seeded ($5 \times 10^4$ cells/well) into wells containing either solely medium or medium with treatment and placed in an incubator at 37° C., 5% $CO_2$, and under humidified conditions for 48 hours. Each condition was performed in duplicate and was subjected to the following protocol:

Apoptosis Analysis as Per Protocol of BD Pharmingen Annexin—VPE Protocol

Reagents include Annexin V-PE (BD Pharmingen, San Diego, Calif.), 7-AAD (BD Pharmingen, San Diego, Calif.), binding buffer (10×: 0.1 M Hepes/NaOH, 1.4 M NaCl, 25 mM $CaCl_2$) [diluted to 1× (9 mL PBS and 1 mL binding buffer) for use in experiment] (BD Pharmingen, San Diego, Calif.), Trypsin-EDTA (Gibco, Grand Island, N.Y.), and desired Media.

Add 0.5 mL trypsin to each well, remove trypsin after approximately 10 seconds, and add 0.5 mL trypsin to each well. Place wells in an incubator, observe level of detachment under microscope after 4 minutes, and gently tap sides and bottom to aid in detachment. When cells detach, neutralize with 0.5 mL serum-supplemented medium. Transfer cell solution to centrifuge tubes, centrifuge cells at 2000 RPM for 5 minutes, aspirate supernatant, resuspend in 6 mL PBS, and split 6 mL into three centrifuge tubes (2 mL each). Centrifuge cells at 2000 RPM for 5 minutes, aspirate supernatant, resuspend in 100 μL binding buffer mix, add 50 μL of Annexin V-PE and 50 μL of 7-AAD in each centrifuge tube, and vortex and place in the dark for 15 minutes. Add 350 μL binding buffer to each tube and perform analysis using the flow cytometer.

A baseline was also created using freshly cultured cells from a flask. The cells were subcultured and washed twice with cold PBS. Subsequently, they were resuspended in 1× binding buffer to a concentration of $1 \times 10^6$ cells/mL. 100 μL of cell suspension were transferred into three test tubes for a total of $1 \times 10^5$ per tube. One tube served as a negative control with no staining introduced. Another was stained with only Annexin V-PE while the final was stained with only 7-AAD. 50 μL of staining solution was placed into each of the tubes. These tubes were then placed in the dark for 15 minutes after which time, 350 μL of binding buffer were added to each. They were then subjected to analysis by flow cytometry prior to the treated and control cells.

Experiment 1: The Effect of Coenzyme Q10 on the Level of Apoptosis in Human Breast Cancer Cells

| MCF-7 Control | MCF-7 Control | MCF-7 Control |
| --- | --- | --- |
| 100 μM CoQ10 | 100 μM CoQ10 | 100 μM CoQ10 |

Seeded 50,000 cells/well
Compare to Baseline of 100,000 cells/sample in Apoptosis Assay (Annexin PI) after 72 hrs.

Experiment 2: The Effect of 2-Propanol Vehicle on the Level of Apoptosis in Melanoma Cells

| SK-MEL 28 Control | SK-MEL 28 Control | SK-MEL 28 Control |
| --- | --- | --- |
| Equivalent Vol. if 50 μM of CoQ10 (1% 2-Propanol) | Equivalent Vol. if 50 μM of CoQ10 (1% 2-Propanol) | Equivalent Vol. if 50 μM of CoQ10 (1% 2-Propanol) |

Seeded 50,000 cells/well
Compare to Baseline of 100,000 cells/sample in Apoptosis Assay (Annexin PI) after 48 hrs.

Experiment 3: The Effect of 2-Propanol Vehicle on the Level of Apoptosis in Neonatal Fibroblasts

| nFIB (P) 6 Control | nFIB (P) 6 Control | nFIB (P) 6 Control |
| --- | --- | --- |
| Equivalent Vol. if 50 μM of CoQ10 (1% 2-Propanol) | Equivalent Vol. if 50 μM of CoQ10 (1% 2-Propanol) | Equivalent Vol. if 50 μM of CoQ10 (1% 2-Propanol) |

Seeded 50,000 cells/well
Compare to Baseline of 100,000 cells/sample in Apoptosis Assay (Annexin PI) after 48 hrs.

Preparation of DMEM/F12 Medium

Materials:
  DMEM/F12 medium (Cat#11330-032 Gibco-Invitrogen Corp, Grand Island, N.Y.)
  Siliconized Sterile Pipette tips—1 mL and 25 mL to be used with PipettMan
  FBS (Fetal Bovine Serum) Supplement (Gibco-Invitrogen Corp, Grand Island, N.Y.)
  PSA (Penicillin Streptomycin Amphoterocin B)—Antimicrobrial Agent Supplement (Cascade Biologics, Inc., Portland, Oreg.)

Procedures:
  Transfer appropriate amount of FBS into DMEM/F12 (e.g., 50 mL FBS in 500 mL medium for 10% serum concentration). Add appropriate amount of PSA to obtain a solution with a final concentration of 100 U/mL Penicillin G, 100 µg/mL streptomycin sulfate, and 0.25 µg/mL Amphotericin B (e.g., 1 mL of 500×PSA in 500 mL medium). Mix by pipetting and inverting bottle. Store at 4° C. until use.

Preparation of EpiLife Medium

Materials:
    Siliconized Sterile Pipette tips—5 mL, 10 mL to be used with PipettMan
    EpiLife Media (M-EPI-500, Cascade Biologicals)
    PSA (500× Penicillin Streptomycin Amphoterocin B)—Antimicrobrial Agent Supplement (R-004-10 Cascade Biologics)
    EDGS (Epidermal Growth Supplement) (S-012-5 Cascade Biologics)

Procedures:
    Transfer one vial of EDGS (5 mL) and PSA (1 mL) into EpiLife Medium resulting in 100 U/mL Penicillin G, 100 µg/mL streptomycin sulfate, and 0.25 µg/mL Amphotericin B (e.g. 1 mL of 500×PSA in 500 mL medium). Mix by pipetting and inverting. Store in 4° C. until use.

Creating a Homogenous Solution of Q10 in Media Protocol

Materials:
    Polystyrene Sterile Pipette tips—200-1000 µM to be used with automatic pipettes
    Siliconized Sterile Pipette tips—10 mL to be used with PipettMan
    15 mL Centrifuge Tubes
    Media
    Coenzyme Q10 (Compound Solutions, Inc., Escondido, Calif.)
    2-propanol (Cat#9083-3, J.T. Baker Chemical Co., Phillipsbury, N.J.)

Procedures:
    Retrieve Q10 stock from −20° C. storage and weigh out approximately 4.4 mg. Transfer Q10 into a 25 mL centrifuge tube. Add 1 mL 2-propanol to centrifuge tube. Vortex and dip in hot water bath (55° C.) to promote dissolution. Add 9 mL of media to centrifuge tube. Vortex and dip in hot water bath (55° C.) if necessary to create a homogenous solution. This results in a 500 µM Q10 solution. Make serial dilutions to treatment concentrations.

Defrosting Cells Protocol

Materials:
    Siliconized Sterile Pipette tips—1 mL, 10 mL to be used with PipettMan
    75 cm$^2$ Cell Culture Flasks
    15 mL Centrifuge Tubes Procedures:
    Acclimate reagents to 37° C. in water bath. Remove cells from liquid nitrogen tank. Keep vial clasped in palm to initiate defrost. Submerge in water bath at 37° C. until completely melted. Transfer cells to a 15 mL centrifuge tube with 10 mL of growth medium. Mix by pipetting. Centrifuge at 2500 RPM for 8 minutes. Aspirate supernatant. Resuspend pellet with appropriate medium. Mix by vortexing and pipetting to homogenize cell suspension. Transfer to 75 cm$^2$ Cell Culture flask(s).

Subculturing Cells Protocol

Materials:
    Siliconized Sterile Pipette tips—5 mL, 10 mL to be used with PipetteMan
    75 cm2 (T75) Cell Culture Flasks
    6 Well Tissue Culture Plates
    15 mL Centrifuge Tubes
    Media
    0.05% Trypsin (Cat#25-052-C1-1× Trypsin-EDTA, Cellgro by Mediatech, Herndon, Va.)

Procedures:
    Acclimate reagents to 37° C. in water bath. Remove medium from cell culture flasks (cells are ready for subculture when approximately 85% confluent). Prime by adding 1-2 mL of trypsin to flask for 30 seconds. Remove trypsin from flask. Add 5 mL of trypsin to flask. Place flask in the incubator at 37° C. for approximately 4 minutes. Remove and observe degree of detachment with microscope. If needed, gently tap flask to aid in detachment. Add 5 mL of serum-containing medium. Mix by pipetting and washing flask with cell suspension. Transfer cell suspension to a 15 mL centrifuge tube. Vortex centrifuge tube. Centrifuge at 2500 RPM for 8 minutes. Aspirate supernatant. Resuspend pellet in appropriate medium. Create a homogenous cell suspension by pipetting and vortexing. Seed cells in new T75 flasks or into wellplates for experimentation.

Counting Cells Protocol

Materials:
    Beckman Coulter® Z1 Cell and Particle Counter (Beckman Coulter, Inc., Fullerton, Calif.)
    Coulter Counter Vials (Beckman Coulter, Inc.)
    Isoton II Diluent (#8546719, Beckman Coulter)
    Coulter CLENZ (#8546929, Beckman Coulter)
    Polystyrene Sterile Pipette tips—20-200 µM, 200-1000 µM to be used with automatic pipettes Procedures:
    After subculture (per subculturing cells protocol described above), pipet the desired volume suspension of cells to count (0.25-1 mL) into Coulter Counter Vial (Beckman, Inc.) using an automatic pipette. Insure that the Beckman Coulter® Z1 Cell and Particle Counter is clean by using Coulter CLENZ (Beckman, Inc., Fullerton, Calif.) to flush. Flush apparatus once with Isoton II Diluent. Add Isoton II Diluent to vial containing cells for a total volume of 10 mL. Use output mode of apparatus to count cells twice to ensure accuracy. Average counts together and calculate total cell number per volume.

Performing in Vitro Experiments Protocol

Materials:
    Polystyrene Sterile Pipette tips—20-200 µM, 200-1000 µM to be used with automatic pipettes
    Siliconized Sterile Pipette tips—5 mL, 10 mL to be used with PipettMan
    75 cm2 Cell Culture Flasks
    6 Well Tissue Culture Plates
    15 mL Centrifuge Tubes
    Coulter Counter Vials (Beckman Coulter, Inc.)
    0.05% Trypsin (Cat#25-052-C1-IX Trypsin-EDTA, Cellgro)

Procedures:
    Acclimate reagents to 37° C. in water bath. Make stock solution of Q10 as per protocol described above for creating a homogenous solution of Q10 in media. Perform serial dilutions to desired concentrations. Place 2 mL media into respective wells. Subculture flasks as per protocol described above for subculturing cells. Resuspend cells with just enough medium to create a homogenous cell suspension (approximately 5 mL). Determine cell concentration as per protocol described above for counting cells. Dilute cell suspension so that the desired amount of cells to seed is contained within 50-100 µL. Seed desired amount of cells into each well. Incubate at 37° C., 5% $CO_2$, and under humidified conditions for desired duration. Aspirate media from wells. Place 0.5 mL trypsin into each well. Incubate for approximately 4 minutes.

Check for degree of detachment under microscope. Swirl, gently tap sides, and gently knock bottom to aid in detachment if necessary. Neutralize trypsin with 0.5 mL medium. Pipette to aid in cell detachment and breaking of clumps. Remove 0.5 mL cell suspension and place in coulter counter vials (Beckman Coulter, Inc.). Count cells as per protocol described above for counting cells.

Inoculation of Animals Protocol

Materials:
  Phospate buffer solution (PBS) (Gibco-Invitrogen Corp, Grand Island, N.Y.)
  Polystyrene Sterile Pipette tips—20-200 μM, 200-1000 μM to be used with automatic pipettes
  Siliconized Sterile Pipette tips—5 mL, 10 mL to be used with PipettMan
  75 cm$^2$ Cell Culture Flasks
  15 mL Centrifuge Tubes
  Coulter Counter Vials (Beckman Coulter Inc.)
  0.05% trypsin (Cat#25-052-C1-1× Trypsin-EDTA, Cellgro)
  Centrifuge tubes (2 mL)
  Anesthetic (Aventin)

Procedures:

Subculture flasks as per the cell subculturing protocol described above. After aspirating supernatant, combine pellets from each flask diluted slightly with PBS with a 5 mL pipette. Dilute final cell suspension to contain approximately ten million cells per 100 μL. Transfer cell suspension to micro-centrifuge tubes (2 mL). Place in ice immediately and leave in ice until injected. Anesthetize mice via an intraperitoneal injection with 0.3 cc Aventin. Inoculate each animal subcutaneously with 0.1 cc cell suspension per site. Transfer any remaining cells into a 15 mL centrifuge tube. Dilute to 10 mL with medium. Centrifuge at 2500 RPM for 8 minutes. Aspirate supernatant. Add 10 mL media to centrifuge tube. Create a homogenous cell suspension by pipetting and vortexing. Seed cells in a T75 flask to ensure experimental cell viability.

Example 2

Effect of a Topical Formulation of Coenzyme Q10 on SK-MEL28 Tumors in Mice

Figure 1:
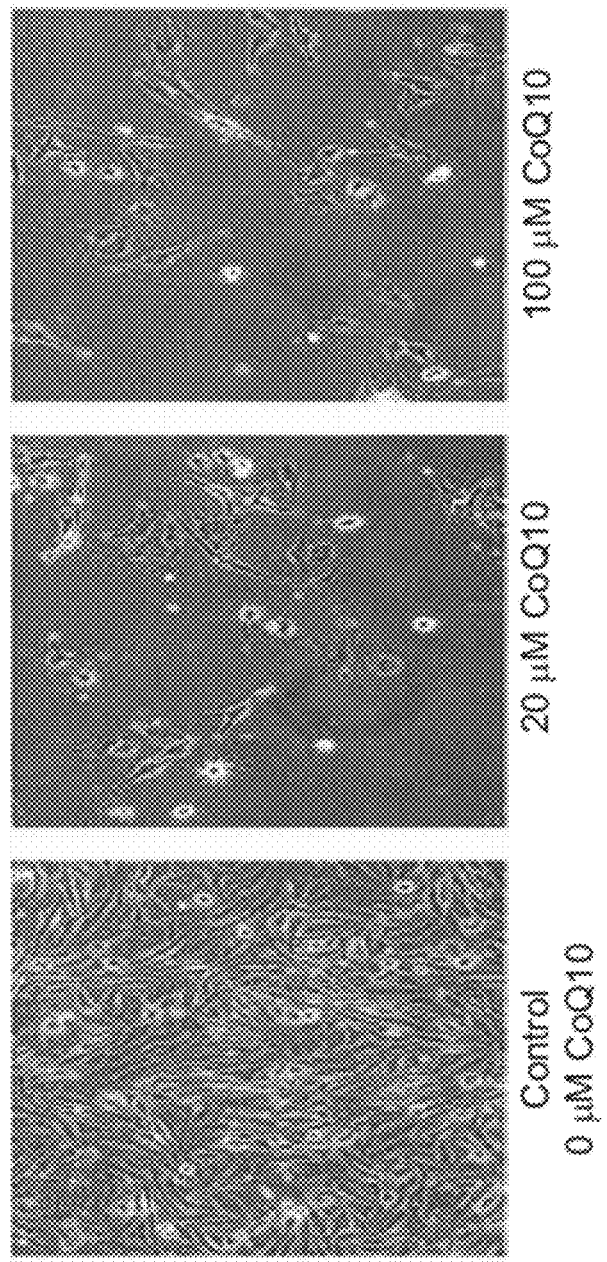
FIG. 1. is a series of photomicrographs showing the effect of CoQ10 on human melanoma cells (SKMEL28) in an in vitro culture.
Figure 2:
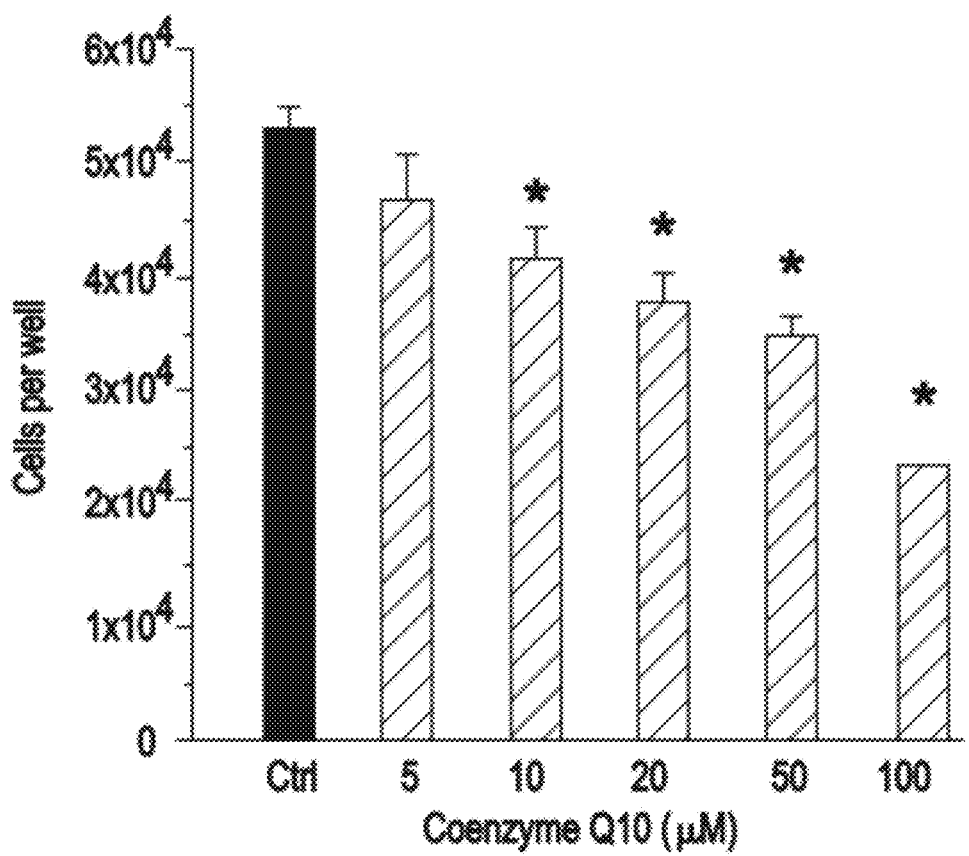
FIG. 2 is a graph showing that CoQ10 reduces the proliferation of a human melanoma cell line (SKMEL28) in a 36 hour in vitro culture.
Figure 3:
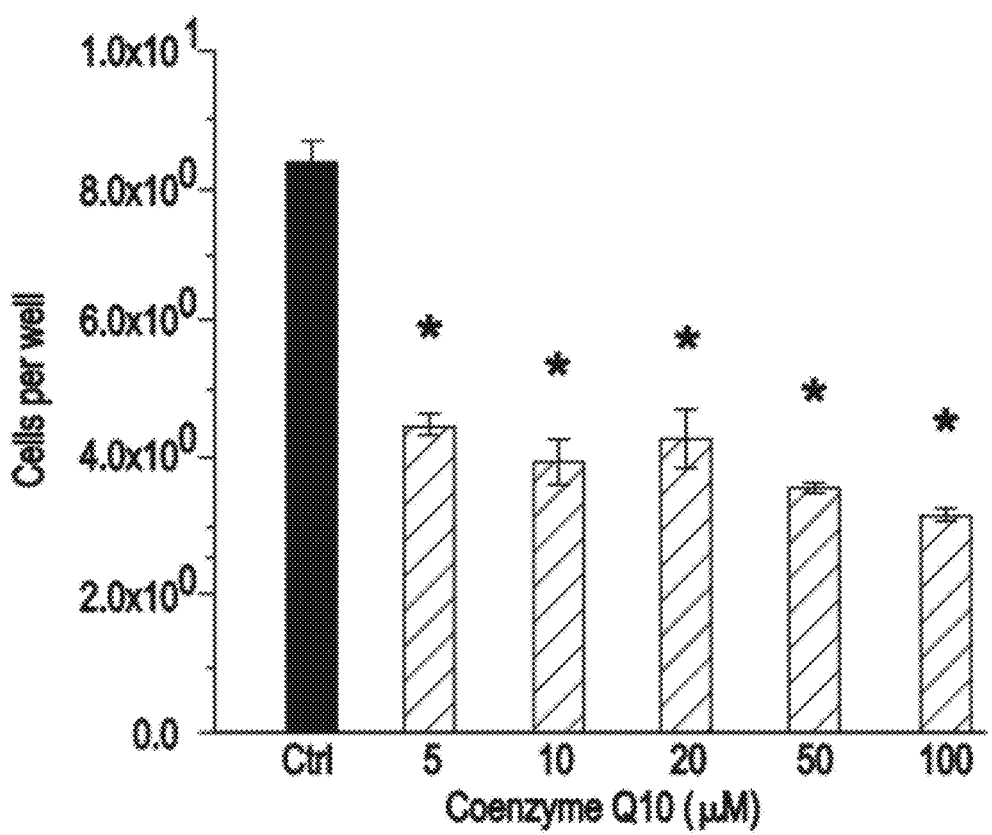
FIG. 3 is a graph showing that CoQ10 reduces the proliferation of a human melanoma cell line (SKMEL28) in a 48 hour in vitro culture.
Figure 4:
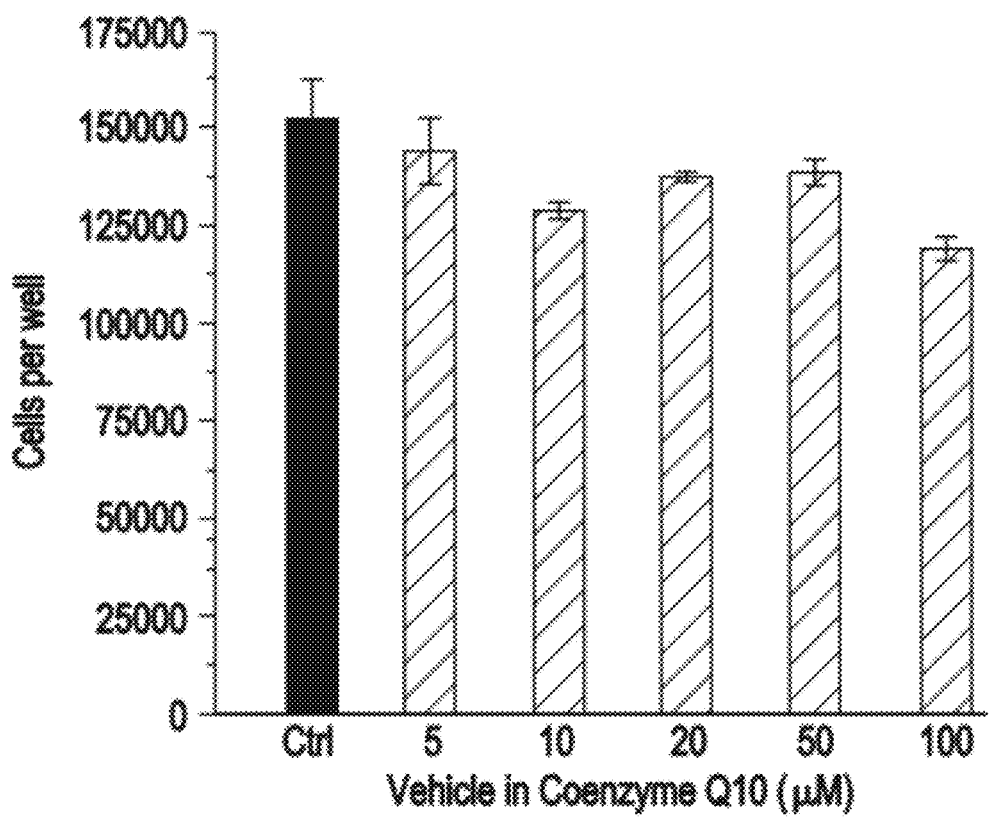
FIG. 4 is a graph showing that the vehicle control does not reduce the proliferation of a human melanoma cell line (SK-MEL28) in a 48 hour in vitro culture.
Figure 5:
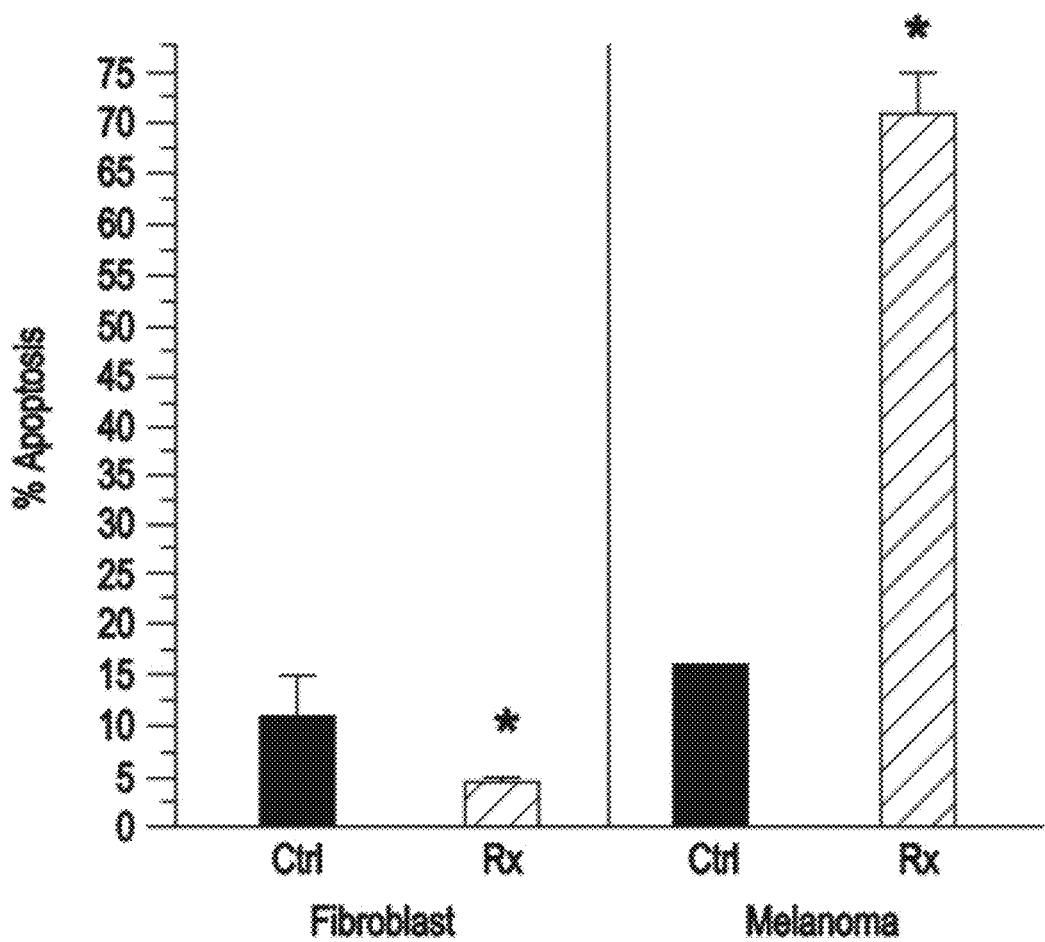
FIG. 5 is a graph comparing the effect of CoQ10 on apoptosis between human melanoma and neonatal fibroblasts in an in vitro culture.
Figure 6:
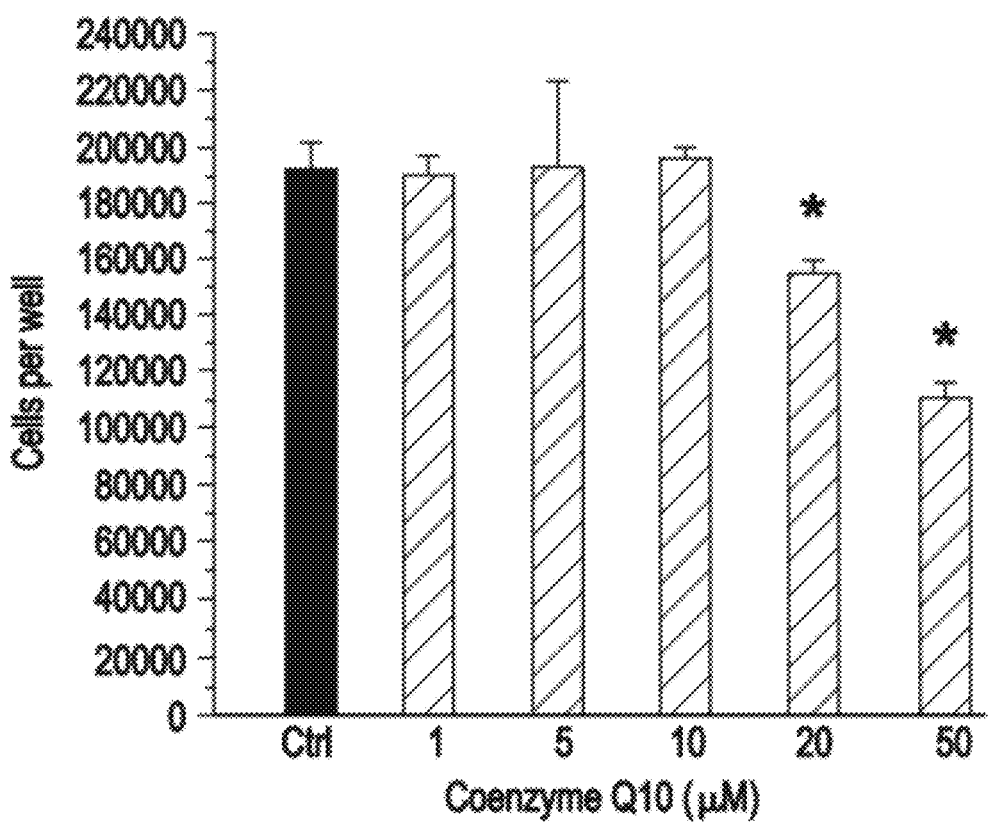
FIG. 6 is a graph showing that CoQ10 reduces the proliferation of squamous carcinoma cells in a 48 hour in vitro culture.
Figure 7:
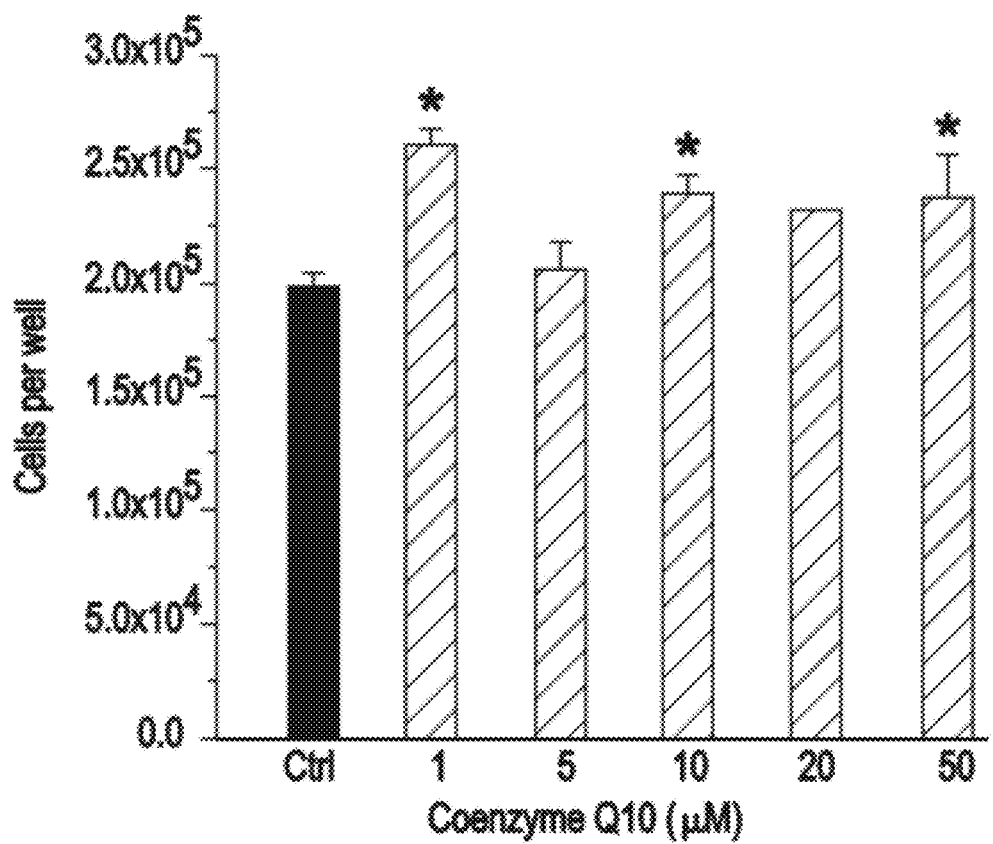
FIG. 7 is a graph showing that CoQ10 increases the proliferation of human neonatal fibroblasts in a 48 hour in vitro culture.
Figure 8:
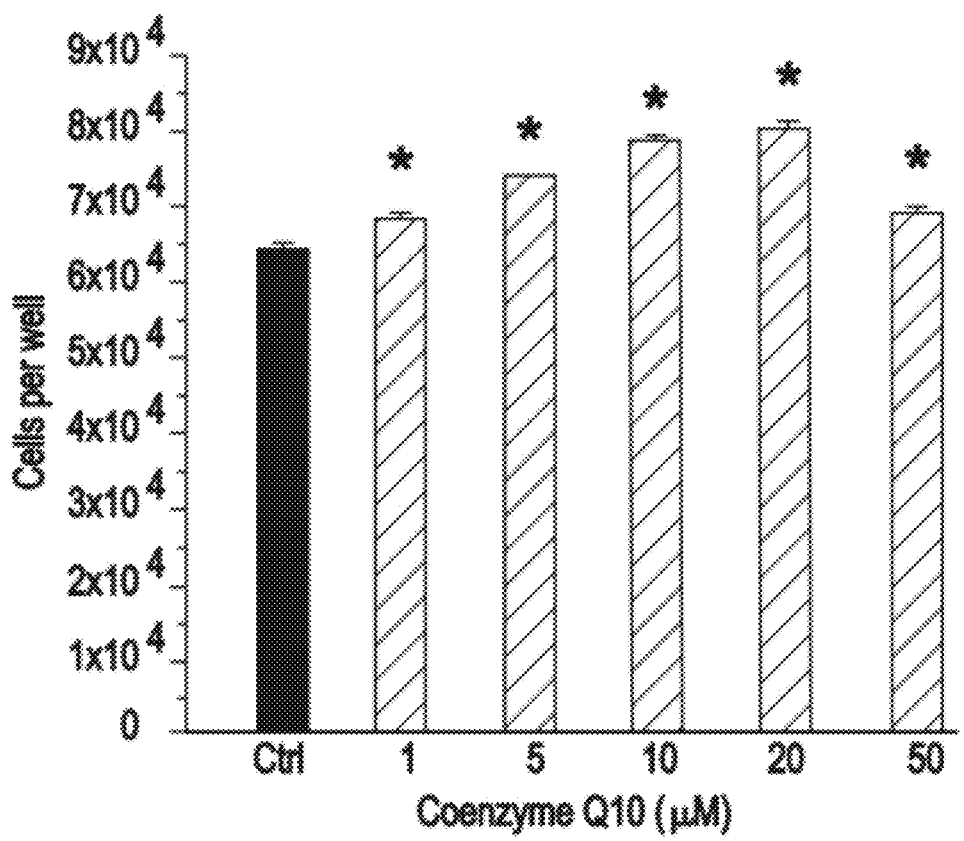
FIG. 8 is a graph showing that CoQ10 increases the proliferation of human neonatal keratinocytes in a 48 hour in vitro culture.
Figure 9:
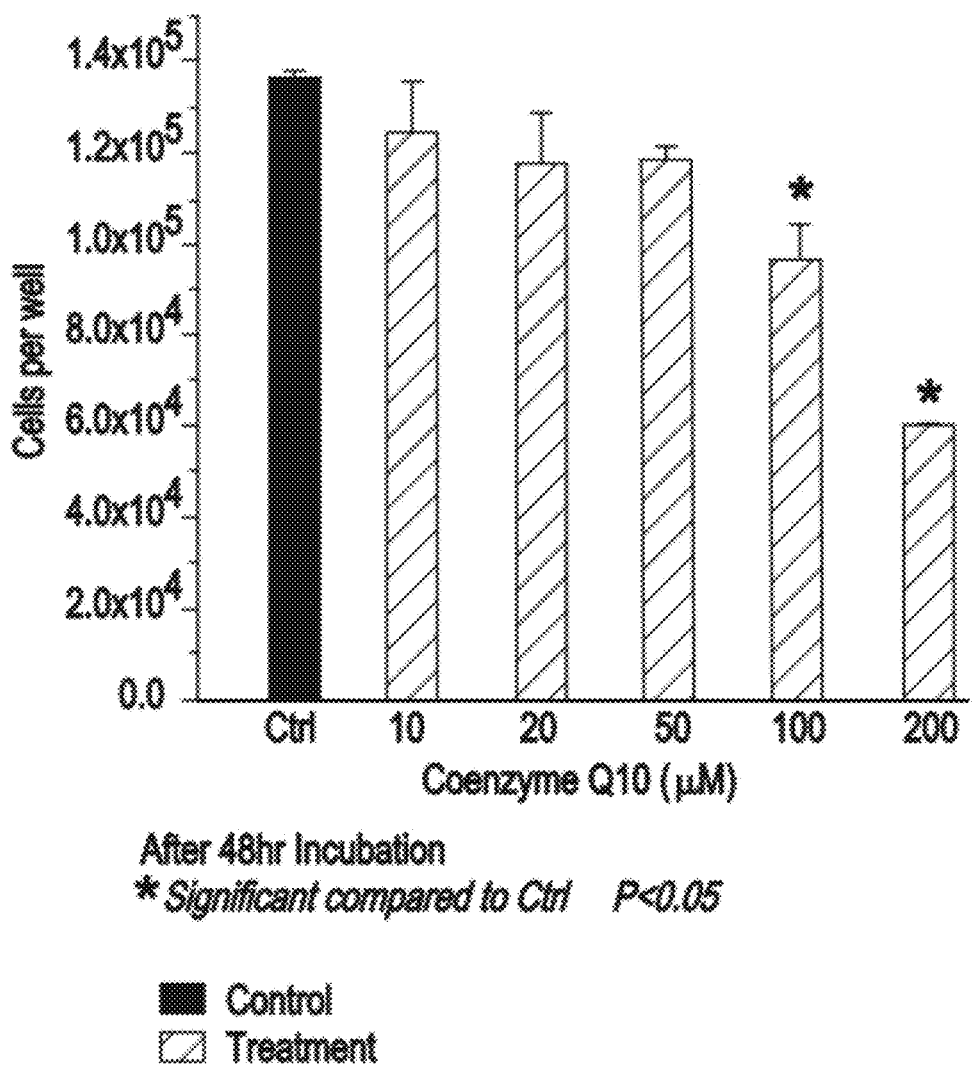
FIG. 9 is a graph showing that CoQ10 reduces the proliferation of a breast adenocarcinoma cell line (MCF-7) in a 48 hour in vitro culture. The MCF-7 cell line expresses the WNT7B oncogene and contains the Tx-4 oncogene.
Figure 10:
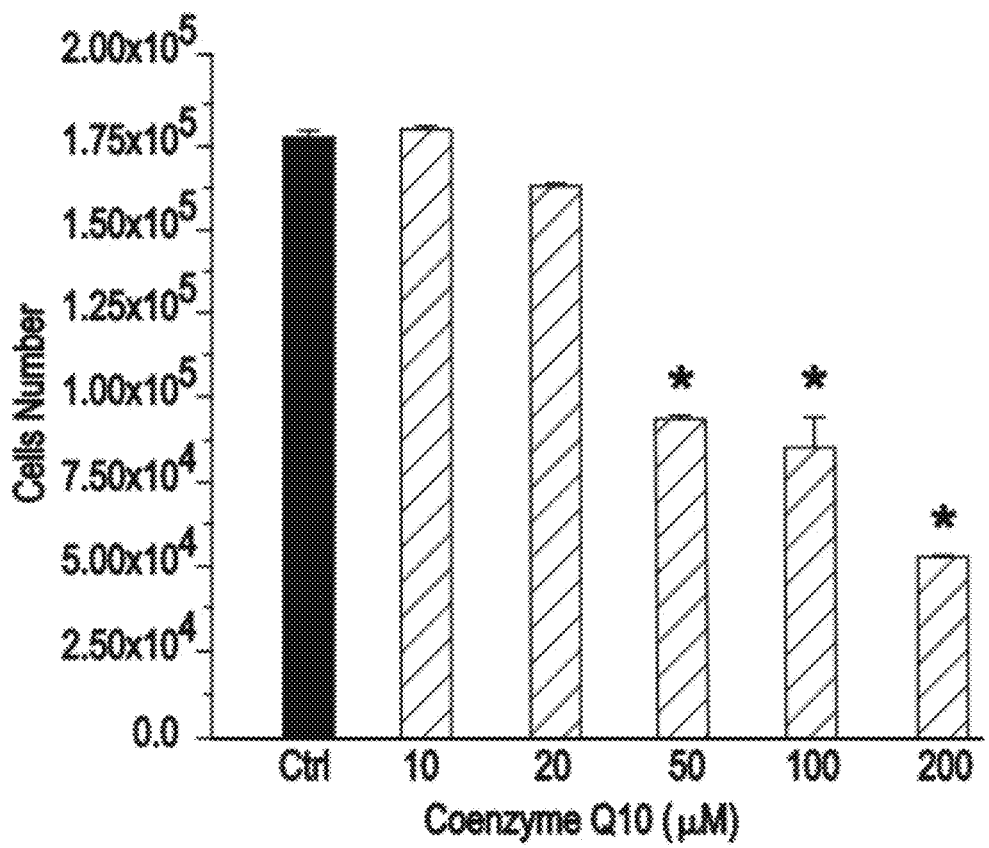
FIG. 10 is a graph showing that CoQ10 reduces the proliferation of a breast adenocarcinoma cell line (MCF-7) in a 72 hour in vitro culture.
Figure 11:
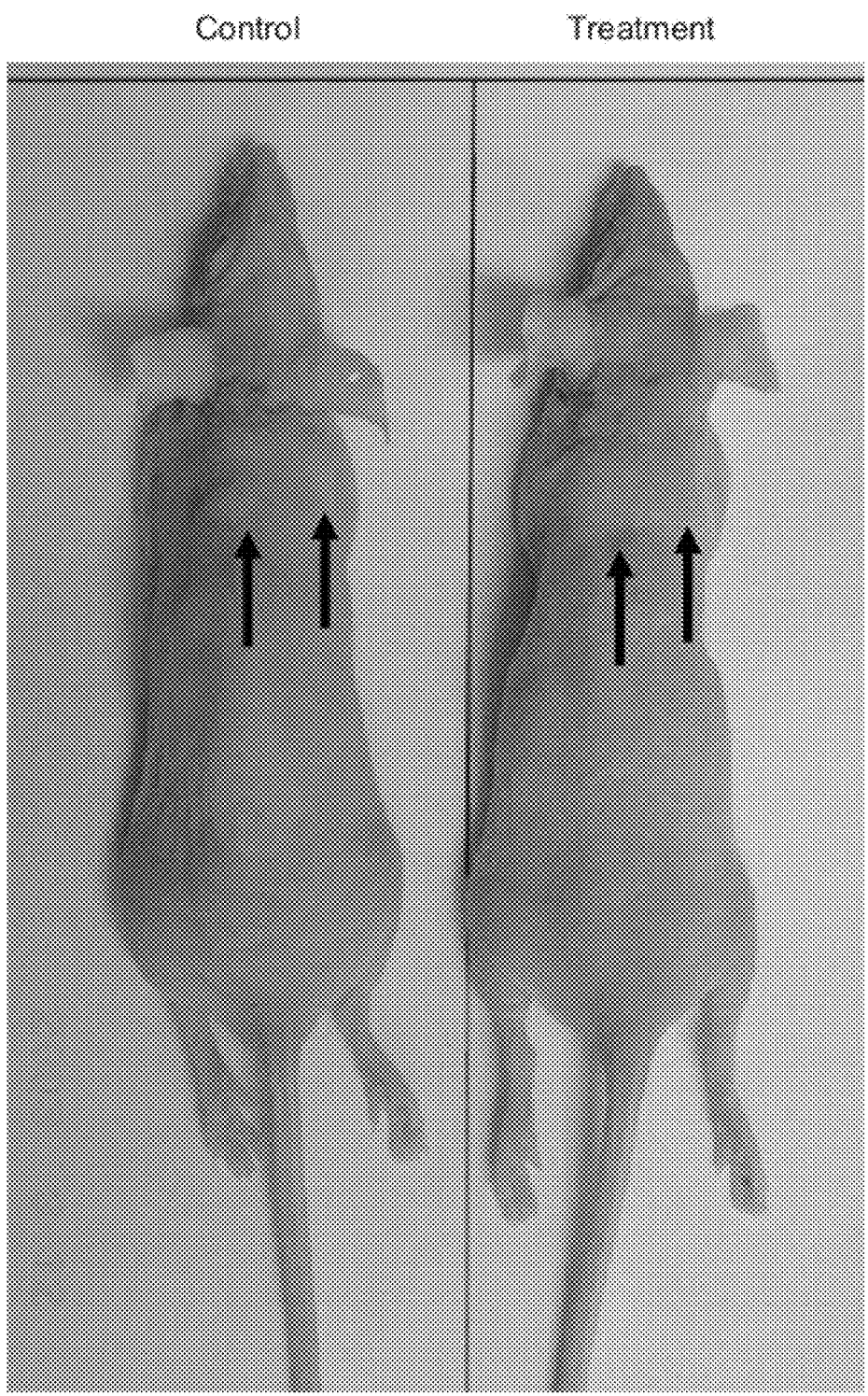
FIG. 11 is a photograph showing induced tumors in control and CoQ10-treated mice after treatment with topical formulation of CoQ10 for 30 days.
Figure 12:
FIG. 12 is a photograph showing induced tumors in control and CoQ10-treated mice after treatment with topical formulation of CoQ10 for 30 days.
Figure 13:
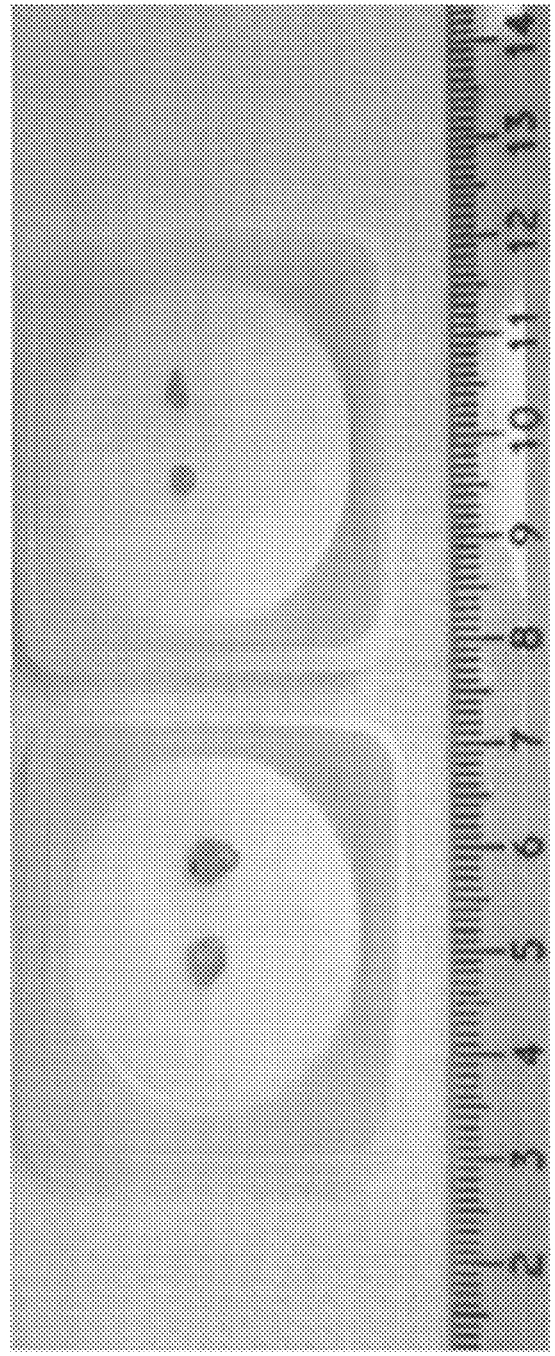
FIG. 13 is a photograph showing tumors excised from control and CoQ10-treated mice.
Figure 14:
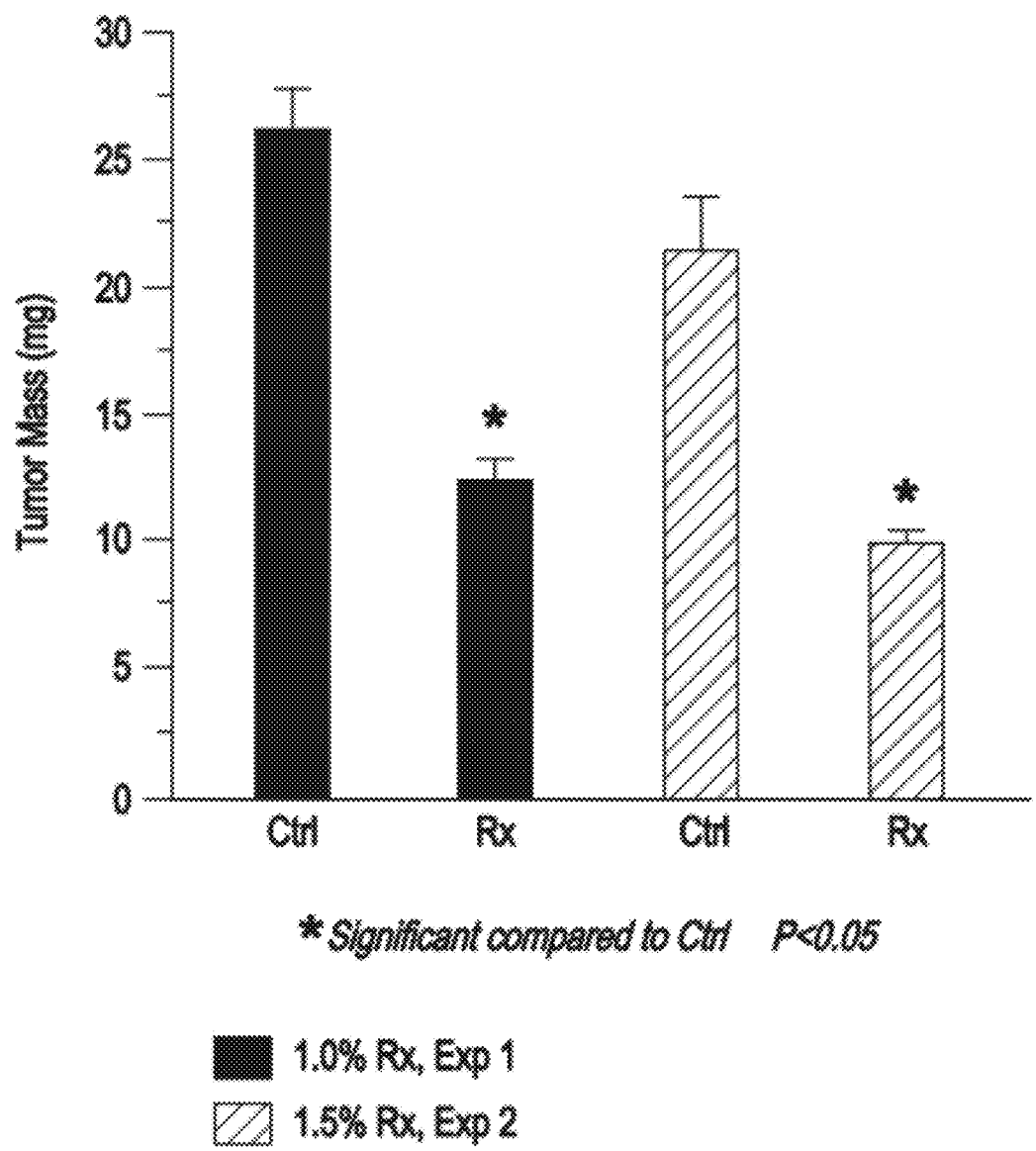
FIG. 14 is a graph showing the effect of CoQ10 administration on tumor size on mice treated topically with CoQ10 (1.0% or 1.5%) or control for 30 days. Average tumor mass in the 1.0% CoQ10 and 1.5% CoQ10 treatment groups decreased by 52.3% and 54.0%, respectively, as compared to the control.
Figure 15:
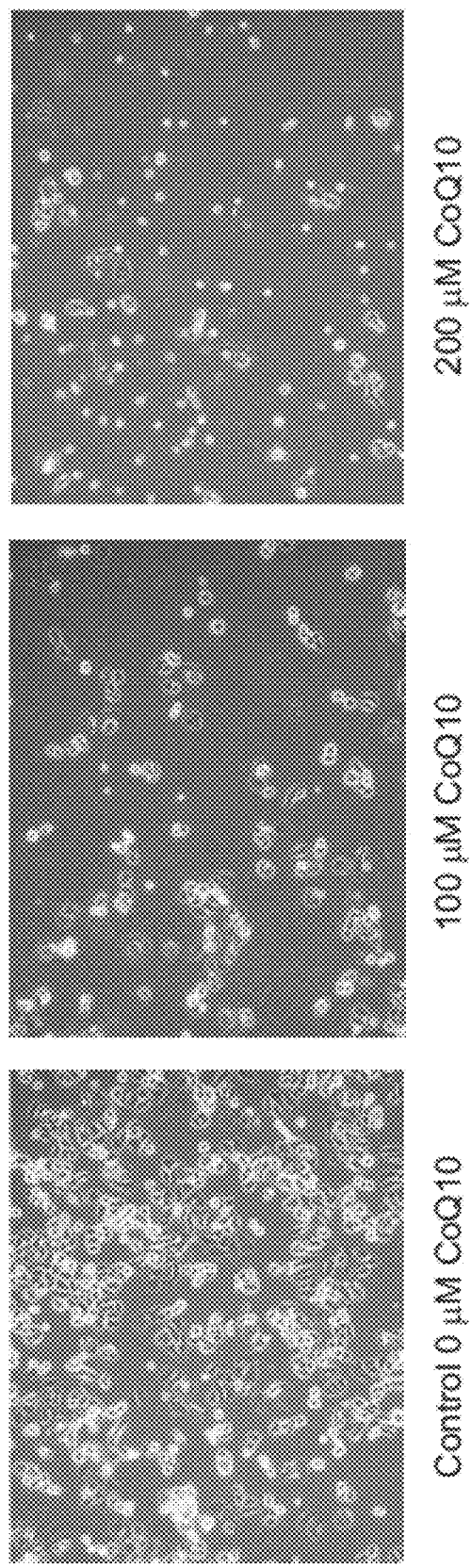
FIG. 15 is a series of photomicrographs showing the effect of CoQ10 on human breast adenocarcinoma cells (SK-BR-3) in an in vitro culture. The SK-BR-3 cell line overexpresses the Her2/c-erb-2 genes, gene product (ATCC).
Figure 16:
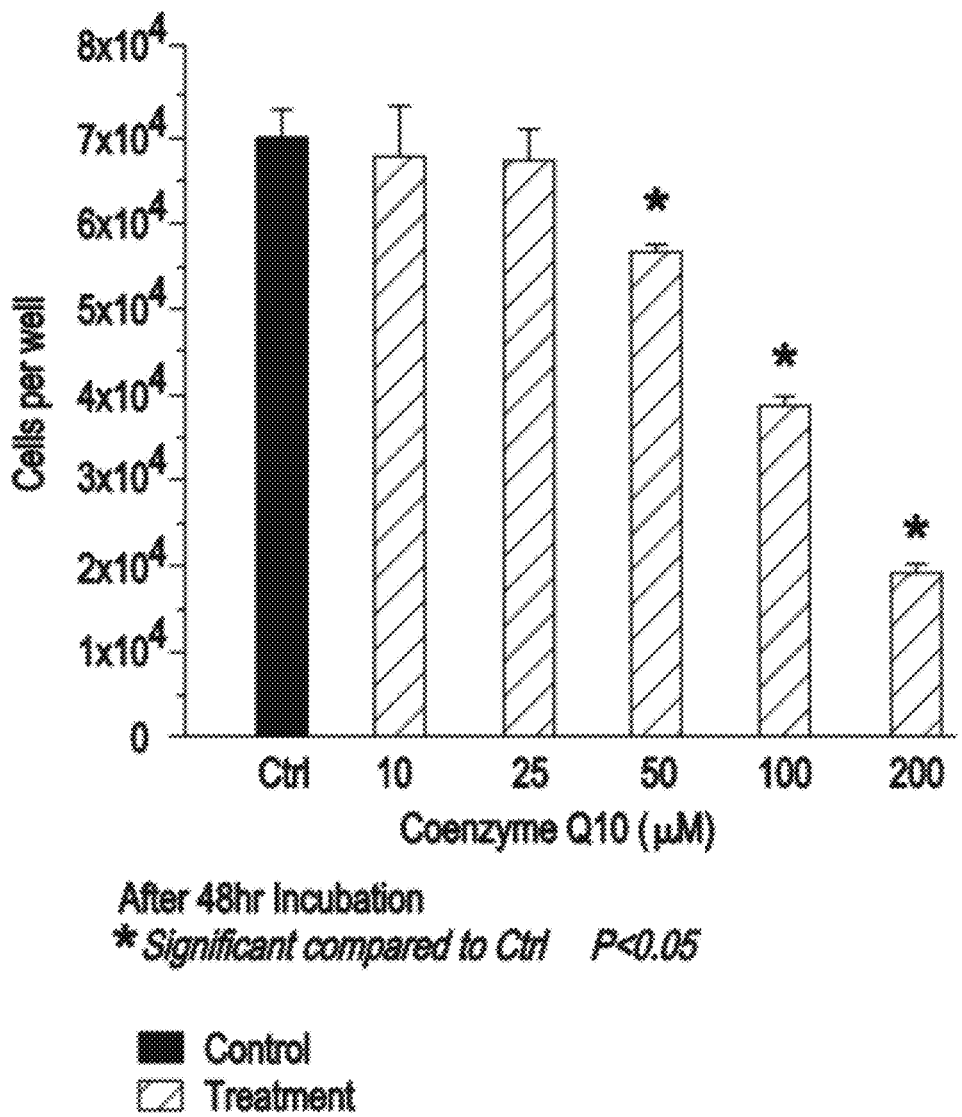
FIG. 16 is a graph showing that CoQ10 reduces the proliferation of a human breast adenocarcinoma cell line (SK-BR-3) in a 48 hour in vitro culture. The SK-BR-3 cell line overexpresses the Her2/c-erb-2 genes gene product (ATCC).
Figure 17:
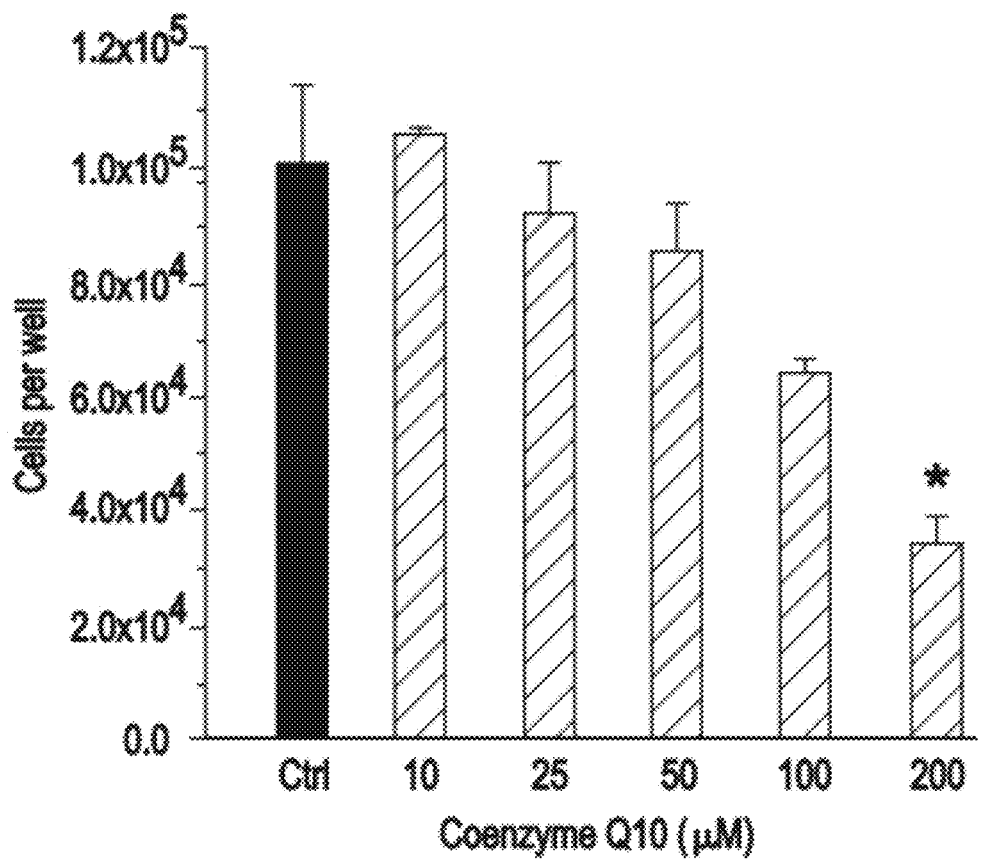
FIG. 17 is a graph showing that CoQ10 reduces the proliferation of a human breast adenocarcinoma cell line (SK-BR-3) in a 72 hour in vitro culture. The SK-BR-3 cell line overexpresses the Her2/c-erb-2 genes gene product (ATCC).
Figure 18:
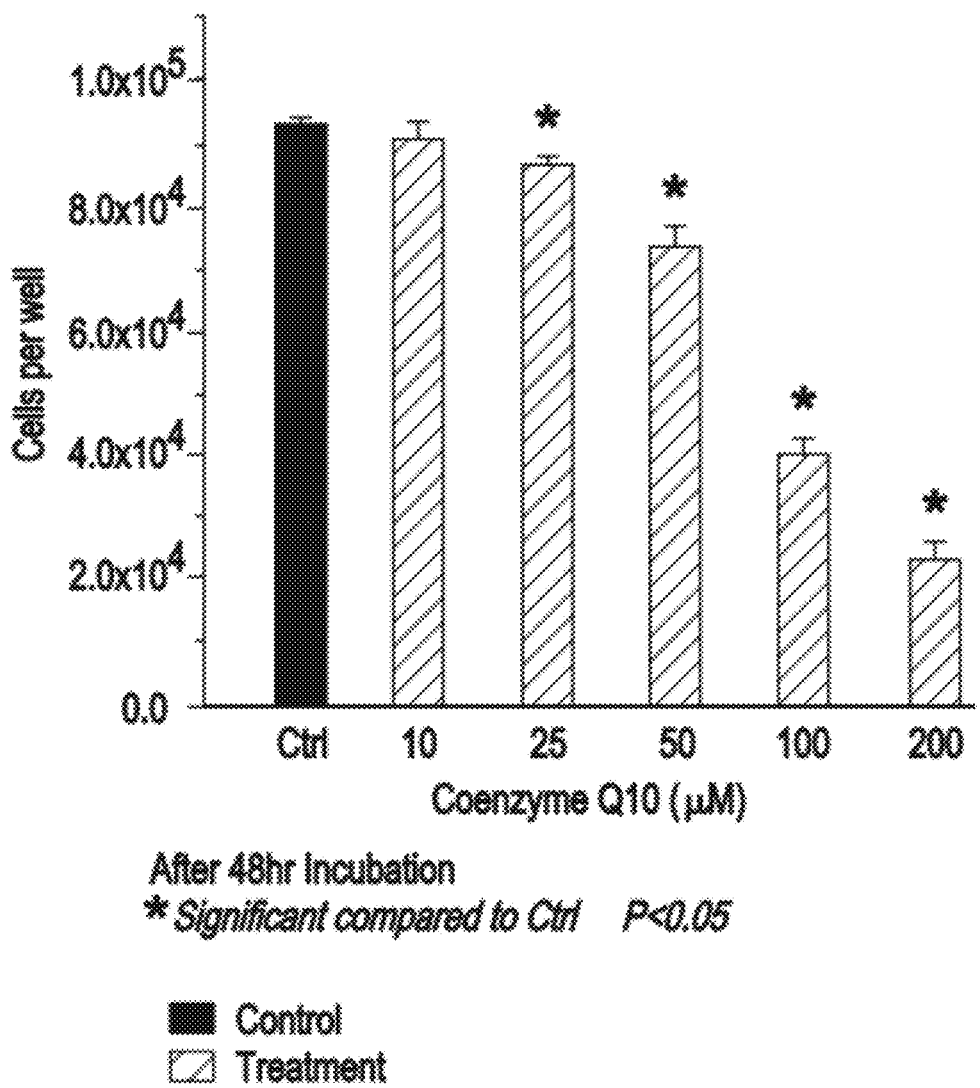
FIG. 18 is a graph showing that CoQ10 reduces the proliferation of a human breast adenocarcinoma cell line (MDA-MB-468) in a 48 hour in vitro culture. The MDA-MB-468 cell line has a mutation in the p53 gene (ATCC).
Figure 19:
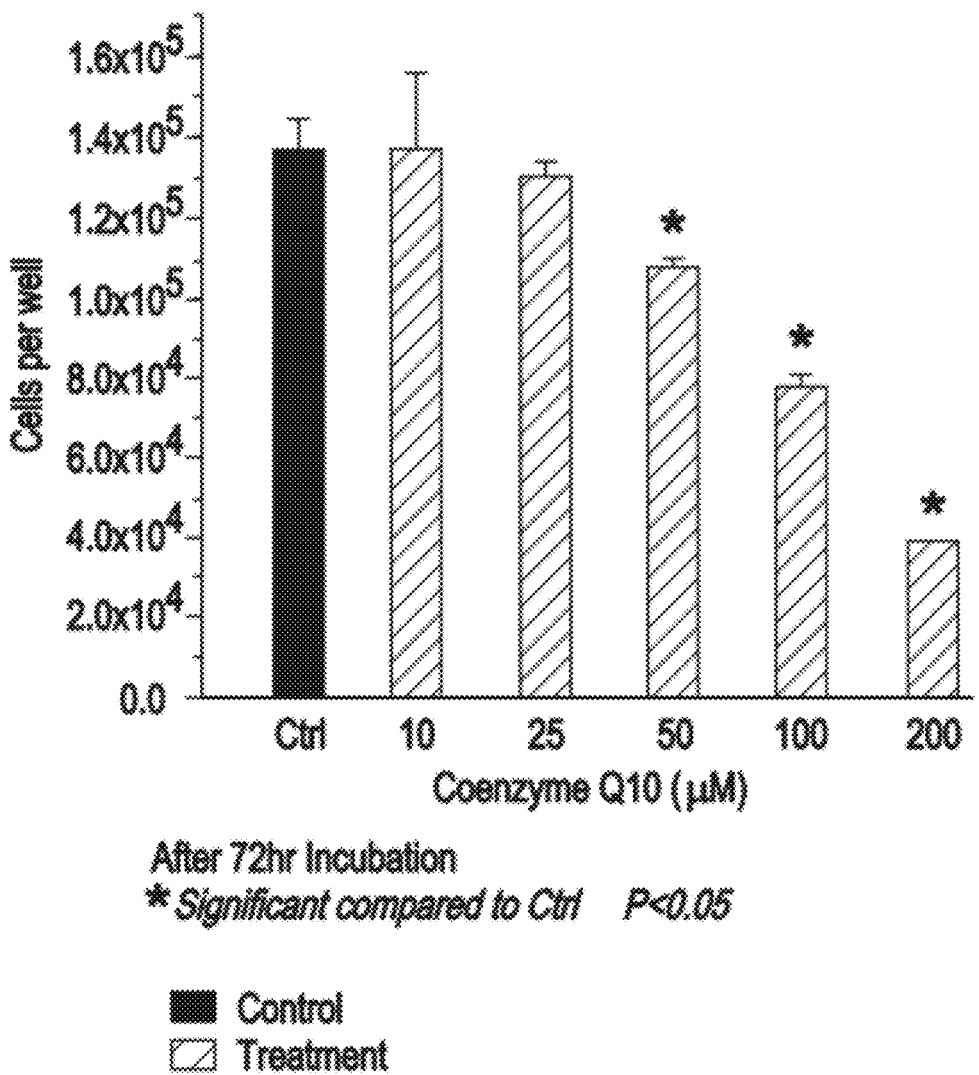
FIG. 19 is a graph showing that CoQ10 reduces the proliferation of a human breast adenocarcinoma cell line (MDA-MB-468) in a 72 hour in vitro culture. The MDA-MB-468 cell line has a mutation in the p53 gene (ATCC).
Figure 20:
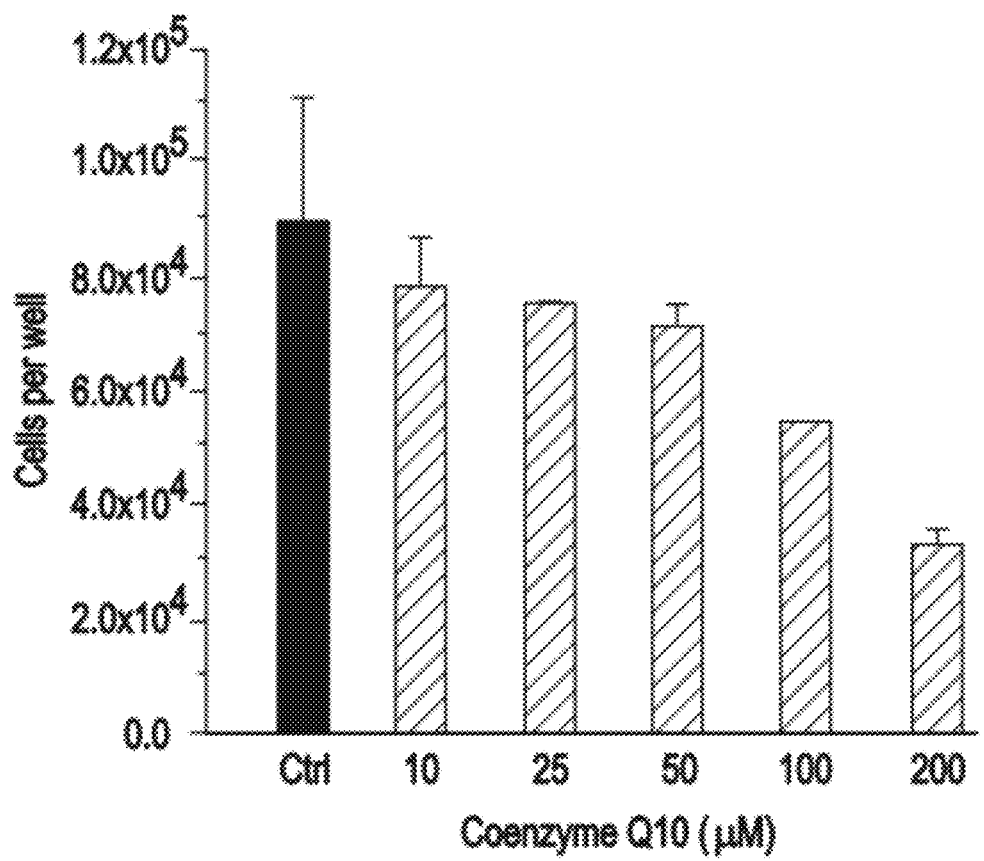
FIG. 20 is a graph showing that CoQ10 reduces the proliferation of a human breast adenocarcinoma cell line (BT-20) in a 48 hour in vitro culture. The BT-20 cell line expresses the WNT7B and WNT3 oncogene (ATCC).
Figure 21:
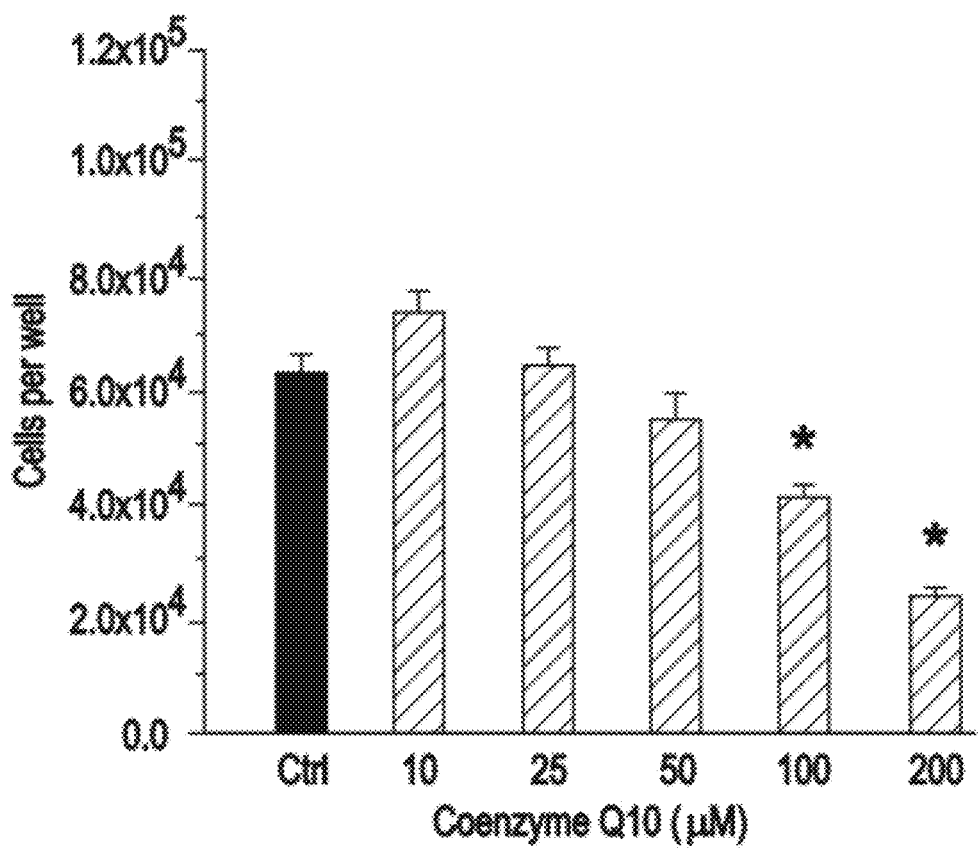
FIG. 21 is a graph showing that CoQ10 reduces the proliferation of a human breast adenocarcinoma cell line (BT-20) in a 72 hour in vitro culture. The BT-20 cell line expresses the WNT7B and WNT3 oncogene (ATCC).

Melanoma tumors were induced in mice by SK-MEL28 injection into the subcutaneous layer. The animal study consisted of both a control and treatment group each containing four mice. The mice were inoculated with two tumors and the graph of FIG. 14 represents the resulting mean mass for the tumors in each mouse. A topical formulation of Coenzyme Q10 (A 1.0% and 1.5% formulation was tested) was applied to the tumors in the treatment group daily for a period of 30 days. After which, the tumors were excised and the mass was determined. The difference in the overall mean mass of the treatment group was significant compared to the control ($P<0.05$).

Example 3

Preparation of Topical CoQ10 Cream

Reagents:
Phospholipon 90G (American Lechitin, Stanford, Conn.)
Glycerol
BHT
Ethanol
MCT
lavender (Sigma-Aldrich)
CoQ10 (Pure Prescriptions, San Diego, Calif.)

Procedure:

10 g of Phospholipon 90G (American Lechitin, Stanford, Conn.) and 5 g of Phospholipon 90H were dissolved in a mixture of 13.3 g of Glycerol (Sigma-Aldrich, St. Louis, Mo.), 0.3 g BHT (Sigma-Aldrich), 9 ml ethanol (Sigma-Aldrich), and 1.5 g MCT (Sigma-Aldrich) at 60° C. 1.1 g of CoQ10 (Pure Prescriptions) were dissolved into the resulting mixture. 65 ml of 1 mM phosphate buffer (pH 8.2) prepared with nitrogen saturated water and 0.2 ml of lavender (Sigma-Aldrich) were added and the mixture was blended in a high speed blender at 12,000 RPM to form a cream. The cream was stored at 4° C. until used.

Example 4

Apoptosis Analysis for JC-1 Stain

Apoptosis was measured using a mitochondrial membrane dye JC-1,5,5',6,6'-tetrachloro-1,1',3,3'-tetraethyl-benzimidazolylcarbocyanine chloride (Molecular Probe, Eugene, Oreg.). Treatments consisting of DMEM-F12 media supplemented with 1×PSA, 5% FBS and 0, 50, 100, and 200 μM concentrations of coenzyme Q10 were prepared in 60×15 mm tissue culture dishes (Costar-Cambridge, Mass.). PC-3 cells were seeded at 500,000 cells per dish and incubated for 24 hours. The cells were trypsinized using 2 mL trypsin-EDTA and subjected to centrifugation at 2,500 rpm for 8 minutes. They were resuspended in 1 mL of Ham's F12 medium lacking serum and phenol red (Cascade Biologics, Inc., Portland, Oreg.) and promptly placed on ice. A 1 mg/ml stock solution of JC-1 was prepared using sterile DMSO and 10 μL was added to each cell suspension while gently vortexing. The cells were incubated at 37° C. for 15 min, diluted with 4 ml of Ham's F12 medium and centrifuged at 600 rpm for 7 min Resuspended in 5 ml of cold PBS (Gibco-Grand Island, N.Y.), the cells were centrifuged again at 600 rpm for 7 min. The cell pellet was then suspended in 1 ml of cold PBS and transferred to nylon filter top flow cytometry tubes covered with foil to prevent light penetration. The samples were analyzed by flow cytometry for changes in uptake of fluorescent dye. The monomer JC-1 displays green fluorescence ($\lambda_{em}=527$ nm) while the J-aggregates display red fluorescence ($\lambda_{em}=590$ nm). Permeabilized mitochondria accumulate the JC-1 monomer dye prior to and during apoptosis.

Other Embodiments

It is to be understood that while the invention has been described in conjunction with the detailed description thereof, the foregoing description is intended to illustrate and not limit the scope of the invention, which is defined by the scope of the appended claims. Other aspect, advantages, and modifications are within the scope of the following claims.

What is claimed is:

1. A method of treating a solid tumor in a subject comprising intravenously administering to the subject having a solid tumor a composition comprising 1% to 20% w/w of Coenzyme Q10 in an amount effective and for a sufficient time to slow the growth of the solid tumor, thereby treating the solid tumor in the subject.

2. The method of claim 1, wherein the composition comprises 1% to 10% w/w of Coenzyme Q10.

3. The method of claim 1, wherein the composition comprises 1% to 5% w/w of Coenzyme Q10.

4. The method of claim 1, wherein the Coenzyme Q10 composition is administered with an additional anti-cancer agent.

5. The method of claim 1, comprising intravenously administering Coenzyme Q10 by continuous infusion.

6. The method of claim 1, wherein the subject has a tumor prior to first administration to the subject of the composition comprising Coenzyme Q10.

7. The method of claim 6, wherein the additional anti-cancer agent is co-administered with the composition comprising Coenzyme Q10 to the subject.

8. The method of claim 6, wherein administration of the additional anti-cancer agent precedes administration of the composition comprising Coenzyme Q10 to the subject.

9. The method of claim 6, wherein administration of the additional anti-cancer agent follows administration of the composition comprising Coenzyme Q10 to the subject.

10. The method of claim 6, wherein the additional anti-cancer agent is an anti-angiogenic agent.

11. The method of claim 6, wherein the additional anti-cancer agent is a chemotherapeutic agent.

12. The method of claim 11, wherein the chemotherapeutic agent is selected from the group consisting of cyclophosphamide, taxanes, busulfan, methotrexate, daunorubicin, doxorubicin, melphalan, cladribine, vincristine, vinblastine, chlorambucil, tamoxifen, taxol, camptothecin, actinomycin-D, mitomycin C, combretastatin, cisplatin, etoposide, verapamil, podophyllotoxin, and 5-fluorouracil.

13. The method of claim 12, wherein the taxane is paclitaxel or docetaxel.

14. The method of claim 1, wherein the solid tumor is a pancreatic tumor.

15. The method of claim 1, wherein the solid tumor is a breast tumor.

16. The method of claim 1, wherein the solid tumor is a lung tumor.

17. The method of claim 1, wherein the solid tumor is a liver tumor.

18. The method of claim 1, wherein the solid tumor is a colon tumor.

19. The method of any one of claims 2-3, 4, 5-13 and 15-18, wherein the subject is a human subject.

* * * * *